United States Patent
Koay et al.

(10) Patent No.: US 9,387,022 B2
(45) Date of Patent: Jul. 12, 2016

(54) VARIABLE ANGLE BONE FIXATION DEVICE

(71) Applicant: DePuy Synthes Products, LLC, Raynham, MA (US)

(72) Inventors: Kenny Koay, West Chester, PA (US); Rod McMillan, West Chester, PA (US); Kenneth Kobayashi, West Chester, PA (US); Rene Haag, West Chester, PA (US); Robert Limouze, West Chester, PA (US); Mike Wahl, West Chester, PA (US); Mirko Rocci, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 298 days.

(21) Appl. No.: 13/927,668

(22) Filed: Jun. 26, 2013

(65) Prior Publication Data
US 2014/0018862 A1     Jan. 16, 2014

Related U.S. Application Data

(63) Continuation-in-part of application No. 13/534,831, filed on Jun. 27, 2012.

(51) Int. Cl.
| | |
|---|---|
| *A61B 17/84* | (2006.01) |
| *A61B 17/86* | (2006.01) |
| *A61B 17/88* | (2006.01) |
| *A61B 17/80* | (2006.01) |
| *A61B 17/56* | (2006.01) |

(52) U.S. Cl.
CPC ............. *A61B 17/8057* (2013.01); *A61B 17/56* (2013.01); *A61B 17/8052* (2013.01); *A61B 17/8061* (2013.01); *A61B 17/84* (2013.01); *A61B 17/86* (2013.01); *A61B 17/8605* (2013.01); *A61B 17/866* (2013.01); *A61B 17/88* (2013.01); *A61B 2017/8655* (2013.01)

(58) Field of Classification Search
CPC ........ A61B 17/56; A61B 17/58; A61B 17/68; A61B 17/80; A61B 17/8052; A61B 17/8057; A61B 17/84; A61B 17/86; A61B 2017/8655; A61B 17/866; A61B 17/88
See application file for complete search history.

(56) References Cited

U.S. PATENT DOCUMENTS

| | | |
|---|---|---|
| 5,556,483 A | 9/1996 | Tahara et al. |
| 5,593,510 A | 1/1997 | Tahara et al. |
| 5,733,287 A * | 3/1998 | Tepic .................... A61B 17/80 606/280 |

(Continued)

FOREIGN PATENT DOCUMENTS

WO     2011/154891     12/2011

OTHER PUBLICATIONS

"Cyprus Anterior Cervical Plate System", Sutgical Technique, Biomet Spine, 2008, 24 sheets.

(Continued)

*Primary Examiner* — Larry E Waggle, Jr.
(74) *Attorney, Agent, or Firm* — Fay Kaplun & Marcin, LLP

(57) ABSTRACT

A bone fixation element includes a threaded head and a shaft extending along a longitudinal axis from a proximal end to a distal end, an outer surface of the head being one of carburized and nitrided and including a first groove extending into an outer surface of the head along a path interrupting the threading and extending along an angle counter to an angle of the threading.

30 Claims, 29 Drawing Sheets

(56) References Cited

U.S. PATENT DOCUMENTS

| | | | |
|---|---|---|---|
| 5,792,282 | A | 8/1998 | Tahara et al. |
| 6,165,597 | A | 12/2000 | Williams et al. |
| 6,206,881 | B1 | 3/2001 | Frigg et al. |
| 6,322,562 | B1 | 11/2001 | Wolter |
| 6,461,448 | B1 | 10/2002 | Williams et al. |
| 7,648,588 | B2 | 1/2010 | Hammond et al. |
| 7,695,502 | B2 | 4/2010 | Orbay et al. |
| 7,776,076 | B2 | 8/2010 | Grady et al. |
| 7,905,909 | B2 * | 3/2011 | Orbay ................ A61B 17/8057 606/280 |
| 7,955,364 | B2 | 6/2011 | Ziolo et al. |
| 8,382,811 | B2 * | 2/2013 | Crook ................ A61B 17/7037 411/412 |
| 2007/0083207 | A1 * | 4/2007 | Ziolo ................ A61B 17/8057 606/287 |
| 2007/0088360 | A1 | 4/2007 | Orbay et al. |
| 2008/0234749 | A1 | 9/2008 | Forstein |
| 2009/0018557 | A1 | 1/2009 | Pisharodi |
| 2009/0143825 | A1 | 6/2009 | Graham et al. |
| 2009/0292318 | A1 | 11/2009 | White et al. |
| 2010/0016858 | A1 | 1/2010 | Michel |
| 2010/0094357 | A1 | 4/2010 | Wallenstein et al. |
| 2010/0100134 | A1 | 4/2010 | Mocanu |
| 2010/0168841 | A1 * | 7/2010 | Furst ................ A61L 27/047 623/1.42 |
| 2011/0022173 | A1 | 1/2011 | Melkent et al. |
| 2011/0077732 | A1 | 3/2011 | Bayer et al. |
| 2011/0106172 | A1 | 5/2011 | Wallenstein et al. |
| 2011/0118795 | A1 * | 5/2011 | Hashmi ................ A61B 17/863 606/308 |
| 2011/0224671 | A1 * | 9/2011 | Koay ................ A61B 17/8052 606/70 |
| 2011/0238122 | A1 | 9/2011 | Gradl |

OTHER PUBLICATIONS

"Forerunner plating System", Featuring SphereLock Technology, Biomet Trauma, 2010, 27 sheets.

* cited by examiner

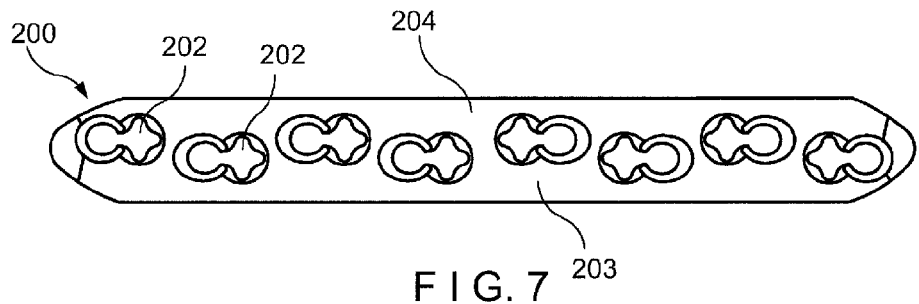
F I G. 7
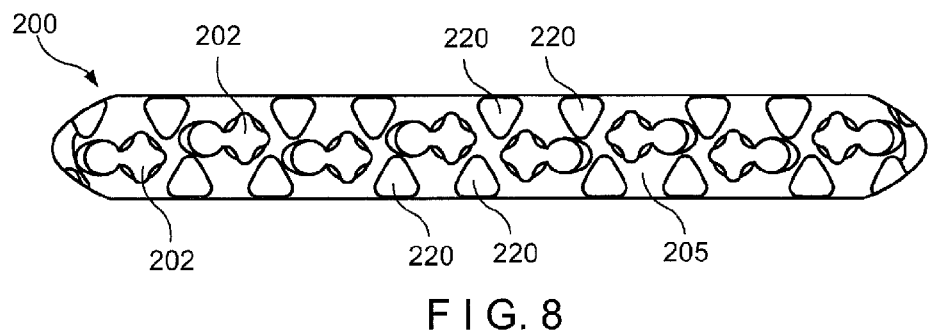
F I G. 8
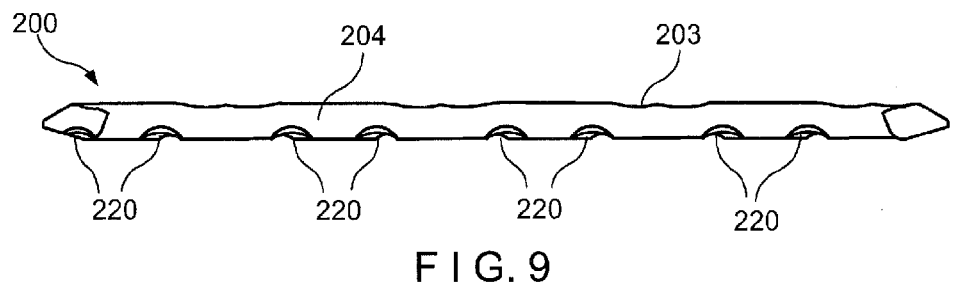
F I G. 9
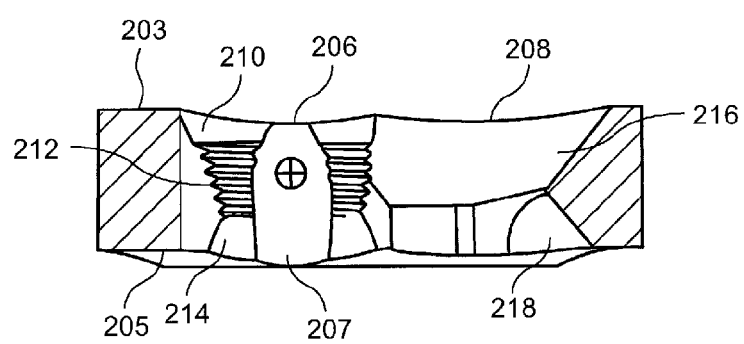
F I G. 10

| Composition | Analysis | Minimum | Maximum |
|---|---|---|---|
| Carbon C [%] | 0,023467 | 0,00 | 0,08 |
| Silicon Si [%] | 0,577813 | 0,00 | 1,00 |
| Manganese Mn [%] | 1,460599 | 0,00 | 2,00 |
| Chromium Cr [%] | 16,90085 | 16,0 | 18,0 |
| Molybdenum Mo [%] | 2,077068 | 2,00 | 3,00 |
| Nickel Ni [%] | 10,37691 | 10,0 | 14,0 |
| Niobium Nb [%] | 0 | 0,00 | 0,00 |
| Titanium Ti [%] | 0 | 0,00 | 0,00 |
| Chromium equivalent [%] | 19,84 | 18,00 | 22,50 |
| Nickel equivalent [%] | 11,81 | 10,00 | 17,40 |

| Composition | Analysis | Minimum | Maximum |
|---|---|---|---|
| Carbon C [%] | 0,023467 | 0,00 | 0,08 |
| Chromium Cr [%] | 16,90085 | 16,00 | 18,00 |
| Molybdenum Mo [%] | 2,077068 | 2,00 | 3,00 |
| Nickel Ni [%] | 10,37691 | 10,00 | 14,00 |
| Copper Cu [%] | 0 | 0,00 | 0,00 |
| Niobium Nb [%] | 0,00 | 0,00 | 0,00 |
| Nitrogen N [%] | 0,0 | 0,00 | 0,10 |
| Chromium equivalent [%] | 18,98 | 18,00 | 21,00 |
| Nickel equivalent [%] | 11,20 | 10,00 | 16,80 |

| Composition | Analysis | Minimum | Maximum |
|---|---|---|---|
| Carbon C [%] | 0,017471 | 0,00 | 0,08 |
| Silicon Si [%] | 0,0,420132 | 0,00 | 0,75 |
| Manganese Mn [%] | 1,677483 | 0,00 | 2,00 |
| Chromium Cr [%] | 17,46971 | 17,00 | 19,00 |
| Molybdenum Mo [%] | 2.771717 | 2,25 | 3,00 |
| Nickel Ni [%] | 14,46273 | 13,00 | 15,00 |
| Niobium Nb [%] | 0 | 0,00 | 0,00 |
| Titanium Ti [%] | 0 | 0,00 | 0,00 |
| Chromium equivalent [%] | 20,24 | 19,25 | 23,13 |
| Nickel equivalent [%] | 15,83 | 13,00 | 18,40 |

| Composition | Analysis | Minimum | Maximum |
|---|---|---|---|
| Carbon C [%] | 0,017471 | 0,00 | 0,03 |
| Chromium Cr [%] | 17,46971 | 17,00 | 19,00 |
| Molybdenum Mo [%] | 2,771717 | 2,25 | 3,00 |
| Nickel Ni [%] | 14,6273 | 13,00 | 15,00 |
| Copper Cu [%] | 0 | 0,00 | 0,00 |
| Niobium Nb [%] | 0,00 | 0,00 | 0,00 |
| Nitrogen N [%] | 0,07 | 0,00 | 0,10 |
| Chromium equivalent [%] | 20,24 | 19,25 | 22,00 |
| Nickel equivalent [%] | 16,64 | 13,00 | 16,05 |

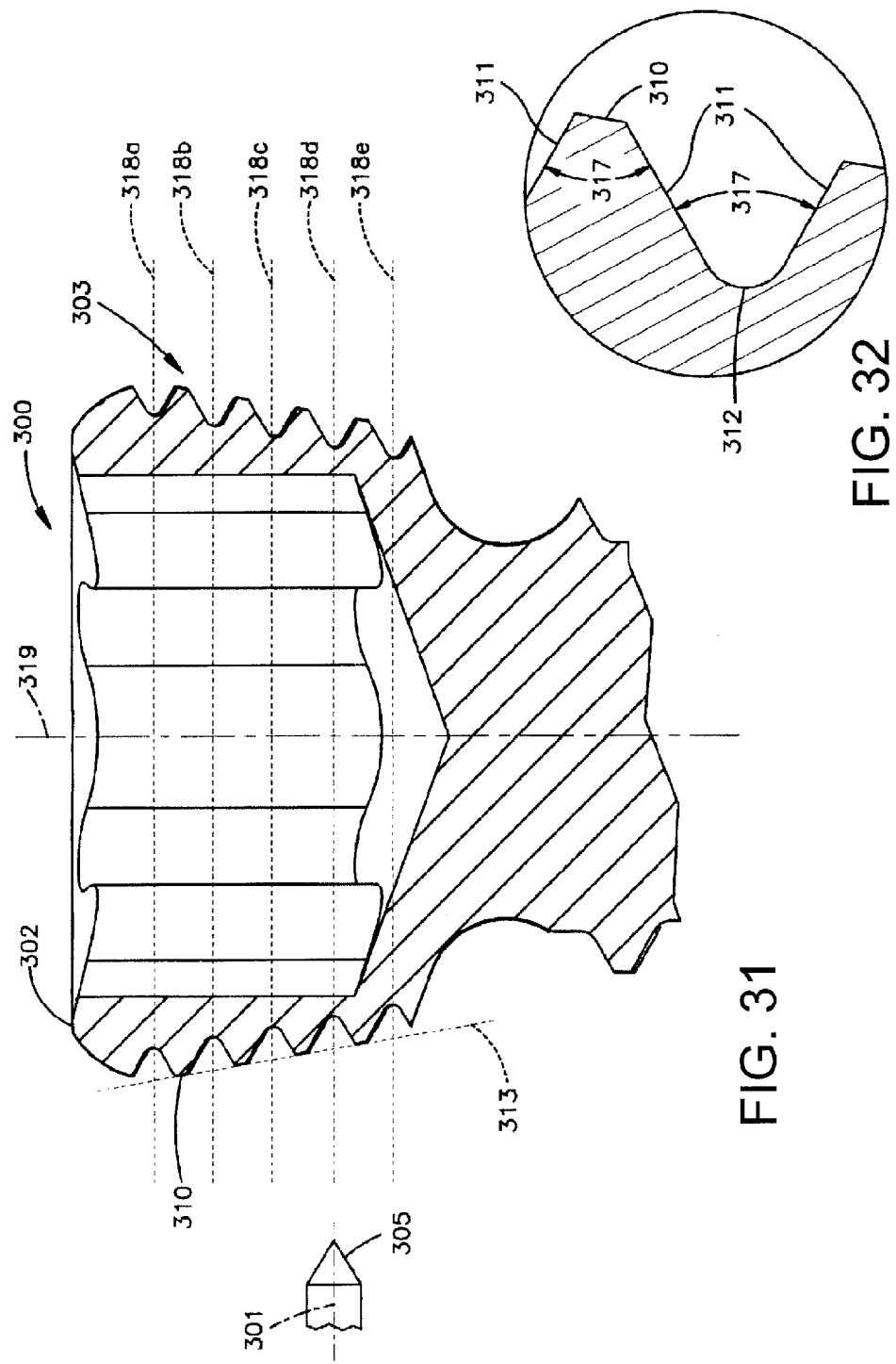

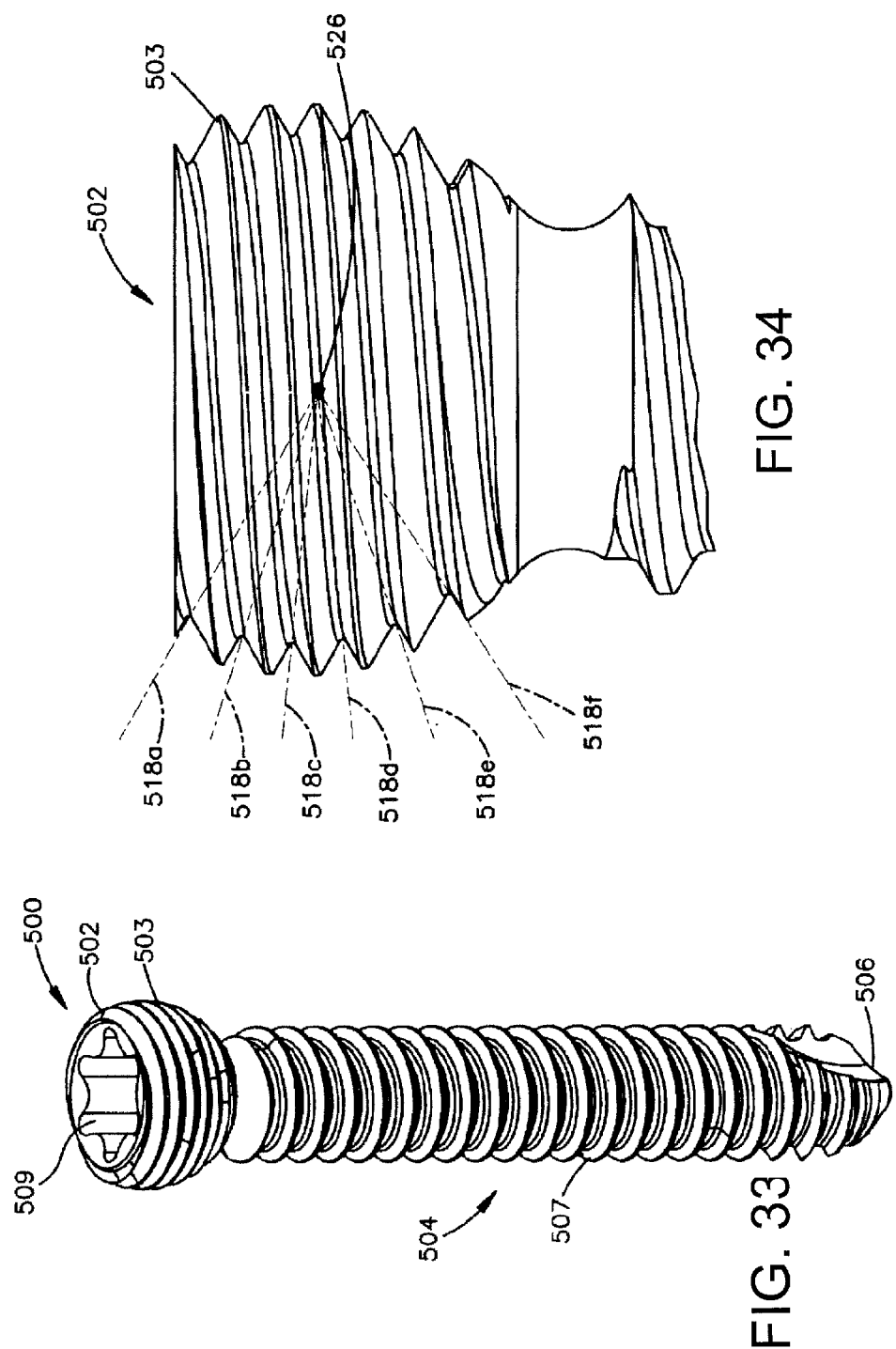

VARIABLE ANGLE BONE FIXATION DEVICE

PRIORITY CLAIM

This application is a Continuation-In-Part of U.S. patent application Ser. No. 13/534,831 filed on Jun. 27, 2012 and entitled "Variable Angle Bone Fixation Device" which is expressly incorporated herein, in their entirety, by reference.

BACKGROUND

Bone fixation plates are often positioned over a fractured or otherwise damaged portion of bone and secured thereto using bone screws inserted through screw holes of the bone fixation plate. The screw holes extend transversely through the bone plate and are sometimes formed with threads to lockingly engage a threaded head of the bone screw. Variable angle screws are often employed which permit a user to insert the screw through the plate at a user-selected angle relative to an axis of the plate hole. However, the engagement threads of the head of such variable angle screw heads with the threading of the plate hole may burr threads of one or both of the bone screw and the bone plate, causing a loss in bone fixation strength. Damage to the bone plate or bone screw in this manner may cause the bone fixation procedure to lose efficacy. Those skilled in the art continue to search for ways to increase the strength of the screw-plate interface in variable angle systems.

SUMMARY OF THE INVENTION

The present invention is directed to a bone fixation element comprising a threaded head and a shaft extending along a longitudinal axis from a proximal end to a distal end, an outer surface of the head being one of carburized and nitrided and including a first groove extending into an outer surface of the head along a path interrupting the threading and extending along an angle counter to an angle of the threading.

BRIEF DESCRIPTION OF THE DRAWINGS

FIG. 7 shows a perspective view of a first surface of a bone plate according to the present invention;

FIG. 8 shows a perspective view of a second surface of the bone plate of FIG. 7;

FIG. 9 shows a lateral view of the bone plate of FIG. 7;

FIG. 10 shows a partial cross-sectional view of a plate hole of the bone plate of FIG. 7;

FIG. 31 is a cross-sectional view of the head of FIG. 30;

FIG. 32 is an enlarged, partial cross-sectional view of the locking bone screw of FIG. 30;

FIG. 33 is a perspective view of a variable-angle locking screw according to the invention;

FIG. 34 is a front elevation view of the head of the variable-angle locking screw of FIG. 33;

DETAILED DESCRIPTION

Figure 1:
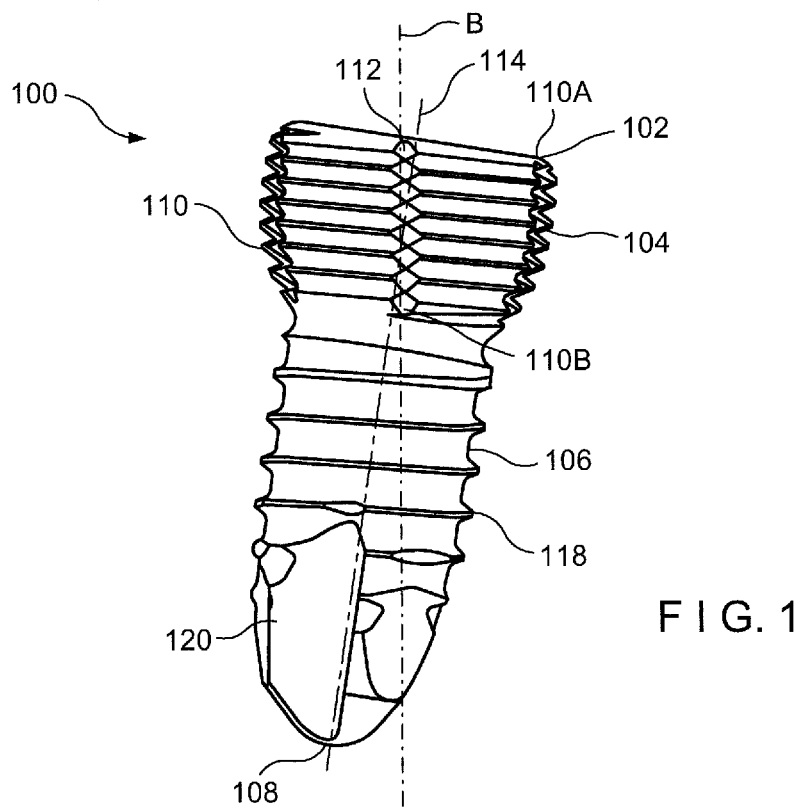
FIG. 1 shows a first perspective view of a bone fixation element according to an exemplary embodiment of the present invention.
Figure 2:
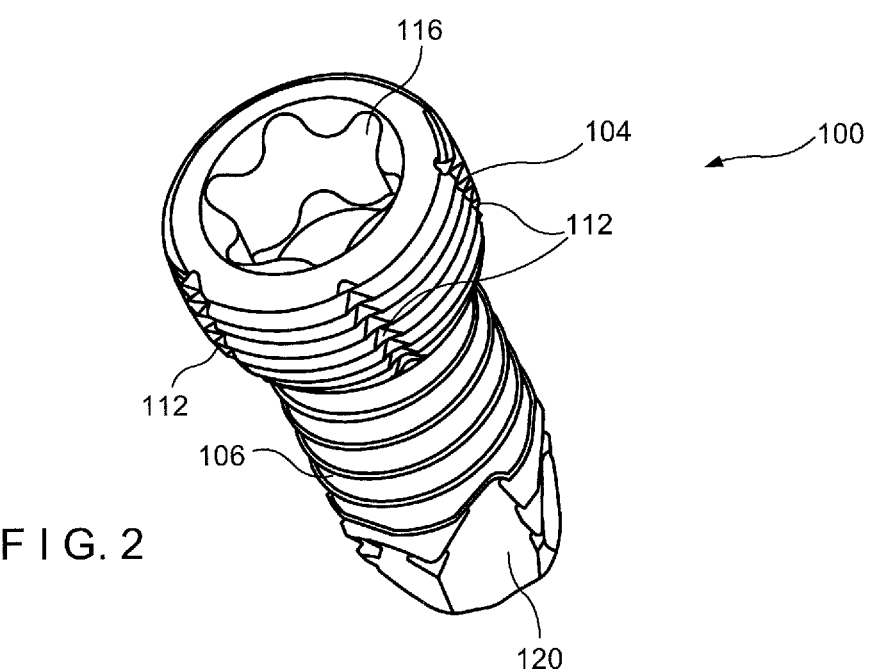
FIG. 2 shows a second perspective view of the bone fixation element of FIG. 1.
Figure 3:
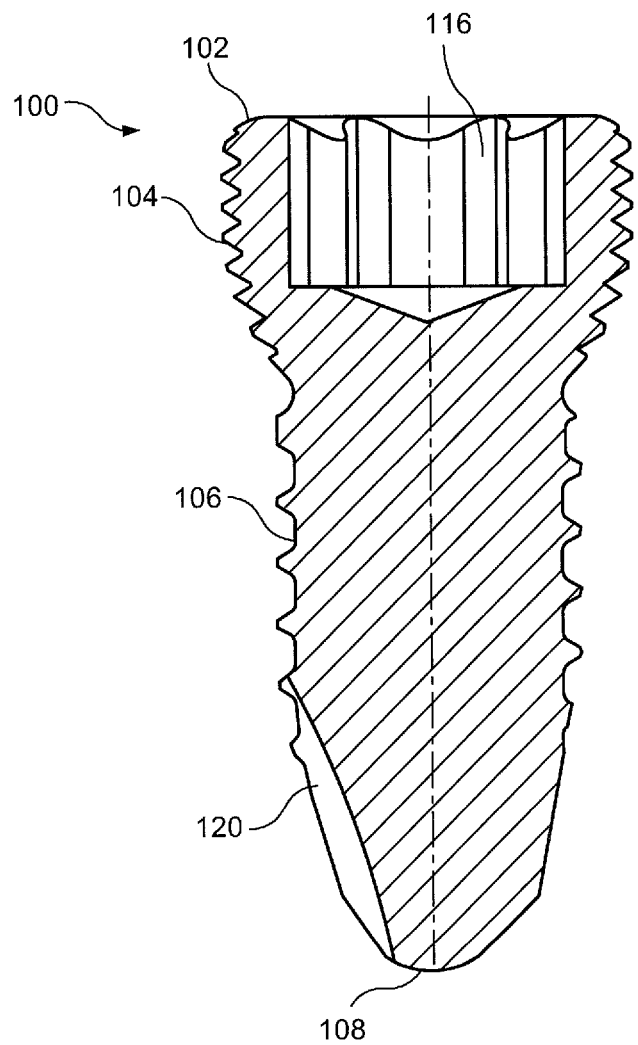
FIG. 3 shows a partial cross-sectional view of the bone fixation element of FIG. 1.
Figure 4:
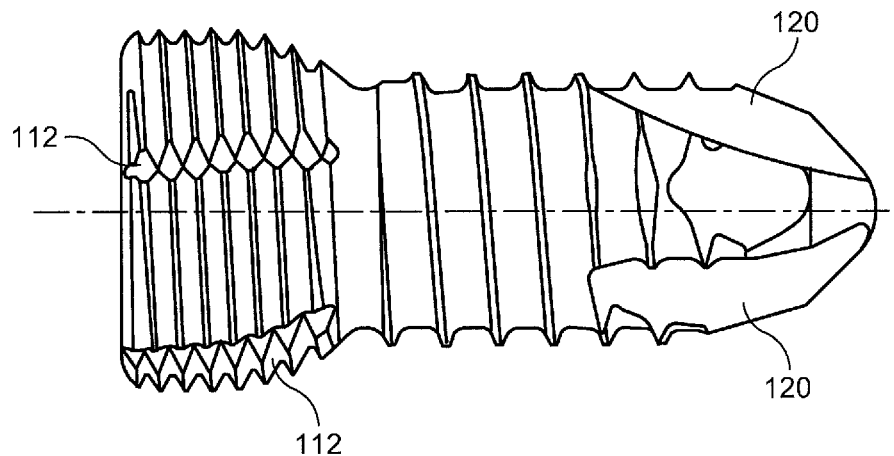
FIG. 4 shows a third perspective view of the bone fixation element of FIG. 1.

The present invention may be further understood with reference to the following description and the appended drawings, wherein like elements are referred to with the same reference numerals. The present invention relates to the stabilization of bones and, in particular, to the stabilization of a fractured or otherwise damaged bone using a bone screw inserted through a bone fixation device (e.g., a bone plate). Exemplary embodiments of the present invention describe a variable angle bone screw having a threaded head and a threaded shaft and having a carburized or nitrided outer surface configured to increase a surface hardness thereof to a desired level. The threaded head comprises one or more grooves extending into an outer surface thereof at an angle relative to a longitudinal axis of the bone screw to aid in alignment of the threads of the head with threads of a variable angle screw hole of the bone fixation device. The shaft comprises one or more notches extending into an outer surface thereof at any angle relative to the longitudinal axis within a permitted range of angulation, as will be described in greater detail later on. In one embodiment, the bone plate may be formed of a metallic alloy exhibiting a hardness within a predetermined range. The bone screw may be carburized or nitrided such that an outer surface of the bone screw has a hardness greater than a hardness of the bone plate. Thus, the exemplary bone screw according to the invention minimizes burring of the screw during insertion into the bone plate while providing a consistent connection strength to the bone and bone plate. Furthermore, the exemplary system according to the invention reduces galling during use while also providing an increased overall strength when compared to standard screws including increased yield strength, ultimate tensile strength and fatigue strength, as those skilled in the art will understand. It should be noted that the terms "proximal" and "distal" as used herein, are intended to refer to a direction toward (proximal) and away from (distal) a user of the device.

Embodiments of the present invention are formed of an implant-grade material having a carburized or nitrided outer surface. Implant-grade materials are those suitable for permanent implantation in the body—i.e., materials which will not have adverse health effects if left within the body for extended periods of time. The carburized or nitrided outer surface is selected to have a hardness greater than that of a bone being treated. In contrast to bone fixation devices which are formed of non-surface treated implant-grade material and often buckle or break when subjected to drilling, chiseling or reaming forces, exemplary bone fixation devices according to the invention are able to withstand increased levels of force without buckling or otherwise deforming. An exemplary bone fixation device according to the invention is formed with a carburized or nitrided outer surface which minimizes the burring of threads or the dulling of sharpened surfaces during insertion into the bone, permitting the continued use of the same bone fixation device without sharpening or replacement. Furthermore, the exemplary implant-grade material of the invention provides tactile feedback to prevent or inhibit breakage thereof. Specifically, the material is formed such that, when excessive force is applied thereto, the device will undergo a degree of bending instead of shattering. Thus, a surgeon or other user may react to the bending and eliminate/reduce a force being applied thereto to prevent breakage. The exemplary carburized or nitrided implant-grade material according to the invention offers the additional advantage that even if a small fragment thereof were separate from the device and inadvertently enter the body, removal would not be necessary, as will be described in greater detail hereinafter. If a device were to fracture, the exemplary material treatment according to the invention renders edges of fractured portions smoother and more rounded as compared to non-treated materials reducing trauma to tissue. Thus, exemplary bone fixation devices according to the invention exhibit increased overall strength when compared to non-surface treated bone fixation devices formed of implant-grade material, including increased yield strength, ultimate tensile strength and fatigue strength, as those skilled in the art will understand.

As shown in FIGS. 1-6, a bone screw 100 according to an exemplary embodiment of the invention extends from a proximal end 102 comprising a head 104 along an elongated shaft 106 to a distal end 108. In an exemplary embodiment, an outer surface of the head 104 is substantially spherical to permit variable angle insertion of the bone screw 100 into a bone fixation device 200, as will be described in greater detail later on. It is noted, however, that the head 104 may be formed in any other shape without deviating from the scope of the invention (e.g., to permit a single-angle insertion of the bone screw 100 into the bone fixation device 200). The outer surface of the head 104 is provided with threading 110 having a pitch configured to lockingly engage threading 212 formed on a walls of an opening 202 extending through the bone fixation device 200, as will also be described in greater detail later on. One or more grooves 112 may be provided on the head 104, each groove 112 extending at least partially into the threads 110 and extending along an axis substantially angled with respect to a longitudinal axis 114 of the bone screw 100. The grooves 112 are configured to interrupt the thread 110, thus creating a plurality of thread starts which aid in alignment of the thread 110 with the threads 212 of the hole 202 in an operative configuration especially when the bone screw 100 is inserted into a bone plate hole angled with respect to an axis of the bone plate hole (i.e., when the threading of the head 104 is misaligned with the threading of the bone plate hole). The grooves 112 further permit the bone screw 100 to advance distally into the bone when rotated via a driving mechanism (not shown).

Each of the grooves 112 may be angled, for example, at an angle of approximately 8.5±1° relative to the line B-B, although any other angle may be used without deviating from the scope of the invention. In an exemplary embodiment, the grooves 112 are angled counter to a direction of the threading 110. For example, as seen in FIG. 1, the line B-B is perpendicular to the path of the threading 110 and the groove 112 is angled relative to the line B-B so that, traveling along the threading 110 from a proximal end 110A thereof toward a distal end 110B, the angle between the threading 110 and the groove 110 is greater than 90° on the proximal side of the thread and less than 90° on the distal side of the thread. In another embodiment, the grooves 112 extend at an angle of approximately 5-85° relative to the line B-B (i.e., 95° to 175° relative to the threading 110). In yet another embodiment, the grooves 112 may extend substantially parallel to the line B-B. The grooves 112 according to this embodiment extend along substantially a complete length of the threading 110. In another embodiment (not shown), the grooves 112 may extend for only a partial length of the threading 110.

Figure 5:
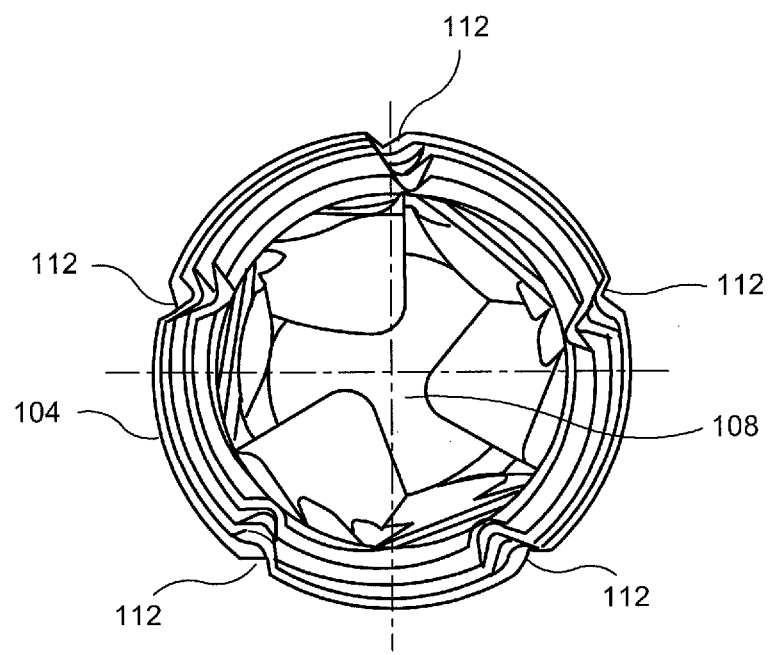
FIG. 5 shows a fourth perspective view of a head of the bone fixation element of FIG. 1.
Figure 6:
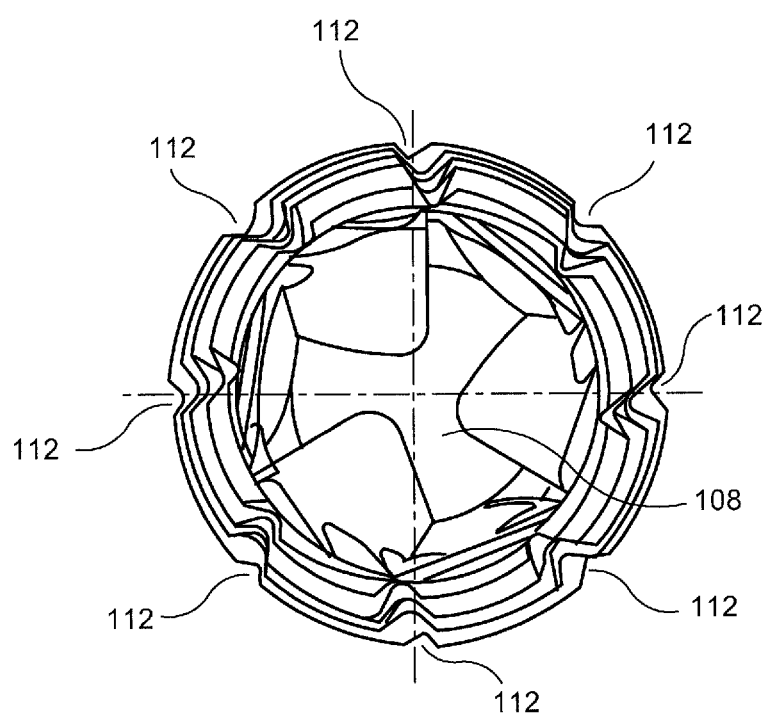
FIG. 6 shows a perspective view of a bone fixation element according to an alternate embodiment of the present invention.

In a first exemplary embodiment of the invention, the bone screw 100 may be formed with five grooves 112 disposed evenly circumferentially about the head 104 and equidistant from one another, as shown in FIG. 5. Specifically, each of the grooves 112 in this embodiment is separated from adjacent grooves 112 by approximately 72°. In another embodiment (not shown), the bone screw 100 comprises six grooves 112 separated from one another by approximately 60°. In yet another embodiment, as shown in FIG. 6, the bone screw 100 may comprise eight grooves 112 separated from one another by approximately 45°.

The head 104 may further comprises a recess 116 extending thereinto from the proximal end 102. The recess 116 is configured to permit engagement with a distal end of a driving mechanism (not shown) for applying torque to the bone screw 100 as would be understood by those skilled in the art. The embodiment of FIGS. 1-6 is depicted with a torx-shaped recess 116. It is noted, however, that any other shape may be employed without deviating from the scope of the invention (e.g., slotted, phillips, square, hexagonal, etc.), as those skilled in the art would understand.

The shaft 106 is provided with threading 118 having a pitch substantially the same as the pitch of the threads 110. In another embodiment of the invention (not shown), the pitch of the threading 118 may be greater than or smaller than the pitch of the threads 110. The threading 118 of the shaft 106 may be formed with two leads, as those skilled in the art will understand. The multi-lead configuration of the threading 118 aids in linear advancement of the bone screw 100 into the bone, as those skilled in the art will understand. As would be understood by those skilled in the art, the length of the shaft 106 is generally selected to conform to requirements of a target procedure. A distal portion of the shaft 106 may comprise one or more notches 120 configured to create a gap in the continuity of the threads 110 and permit self-tapping of the bone screw 100, as those skilled in the art will understand. The distal portion of the shaft 106 may taper to a smaller diameter at the distal end 106 to, for example, aid in insertion. The distal end 106 may be sharpened or blunt as desired.

The bone screw 100 may be formed of a material selected to have a greater hardness that a material of a bone fixation device 200 with which it is to be employed. Specifically, the bone screw 100 may be formed of one of stainless steel and CCM (Co-28Cr-6Mo Alloy). The bone screw 100 may then be carburized or nitrided to further increase a surface hardness thereof to approximately 68 HRC or more, as those skilled in the art will understand. In an exemplary embodiment, the hardness of the bone screw 100 may be approximately 67-74 HRC and, more particularly, 67.5-70.3 HRC. In contrast, the bone fixation device 200 may be formed of commercially pure Titanium grades 1, 2, 3 and 4, Ti-6Al-7Nb, Ti-6Al-4V, Ti-6Al-4V ELI, Ti-15Mo, CCM (Co-28Cr-6Mo Alloy), stainless steel or another material different than the material of the bone screw 100. As those skilled in the art will understand, a hardness of the bone fixation device 200 may be between approximately 75 HRB (e.g., for a CP1 material) and approximately 45 HRC (e.g., for a CCM material). This configuration minimizes burring of the threads 110 of the bone screw 100 as they are inserted into the bone fixation device 100 while also increasing a holding strength of the bone fixation system in the bone.

The bone fixation device 100 is formed of an implant grade material selected from a group including, but not limited to, implant quality austenitic stainless steel (e.g., 316L, 22-13-5, Biodur 108), cobalt alloys such as CCM (Co-28Cr-6Mo Alloy), MP35N, L605, ASTM-F-1058 and Elgiloy and Titanium and its alloys such as Ti-6Al-4V, Ti-6Al-7Nb and Ti-15Mo. The selected material is preferably non-magnetic so that, if fragmented and left within the body, the patient may undergo magnetic resonance imaging ("MRI") without suffering adverse effects, as those skilled in the art will understand. Furthermore, the carburized/nitrided treatment of the selected material results in fragmented portions that do not contain sharp edges, preventing trauma to surrounding tissue. While the selected material of the bone fixation device 100 is substantially soft as compared to conventional devices, the addition of a carburized or nitrided outer surface increases a rigidity thereof to a level greater than that of a bone within which it is to be employed and substantially greater than conventional bone fixation devices. Specifically, the bone fixation device 100 may have a surface hardness of approximately 68 HRC or more, as those skilled in the art will understand. In an exemplary embodiment, the hardness of the bone fixation device 100 may be approximately 67-74 HRC and, more particularly, 67.5-70.3 HRC. As those skilled in the art will understand, this configuration minimizes dulling of the threading 110, 118 after prolonged use while also easing insertion of the bone fixation device 100 into the bone in accordance with an exemplary reaming procedure. During operation, the carburized or nitrided outer surface of the bone fixation device 100 aids in cutting through bone and/or metal without seizing or losing sharpness. The exemplary carburized or nitrided outer surface of the bone fixation device 100 permits use thereof in bone without the risk of excessive burring or warranting replacement due to said burring. Furthermore, the carburized or nitrided material of the present invention provides an increased rigidity to the bone fixation device without having to enlarge or otherwise change a geometry of the device.

In one embodiment, the bone fixation device may be formed of a Biodur 108 alloy which is an essentially nickel-free austenitic stainless alloy. The alloy contains a high nitrogen content to maintain its austenitic structure. As a result, BioDur 108 alloy has improved levels of tensile and fatigue strength, as compared to nickel-containing alloys such as Type 316L (ASTM F138), 22Cr-13Ni-5Mn alloy (ASTM F1314), and 734 alloy (ASTM F1586). The resistance of BioDur 108 alloy to pitting and crevice corrosion is superior to Type 316L alloy and equivalent to the 22Cr-13Ni-5Mn and 734 alloys. BioDur 108 alloy is produced by the Electro-Slag Remelting (ESR) process to assure its microstructural integrity and cleanness. The alloy is non-magnetic and essentially free of ferrite phase. BioDur 108 alloy possesses a high resistance to corrosion due to its high levels of chromium and nitrogen and its molybdenum content. The alloy exhibits excellent resistance to pitting and crevice corrosion. BioDur 108 alloy was designed to have corrosion resistance equivalent to or greater than the nickel-containing alloys, 22Cr-13Ni-5Mn (ASTM F1314) and 734 (ASTM F1586). The corrosion resistance levels of these alloys are superior to Type 316L alloy (ASTM F138). Critical crevice temperatures of 50° F. (10° C.) were measured (per ASTM G48, Method D) in BioDur 108 alloy specimens. Critical temperatures of 41° F. (5° C.) were measured in identically prepared specimens of the 22Cr-13Ni-5Mn alloy. Under these test conditions, the critical temperature of the Type 316L alloy would be below 32° F. (0° C.). The relative corrosion resistances of BioDur 108 alloy and the comparative alloys were confirmed with anodic polarization testing in Ringer's solution at 98.6° F. (37° C.). The BioDur 108 alloy test article was concluded to be non-cytotoxic, non-toxic, non-hemolytic, negligibly irritant, exhibits no signs of toxicity, were observed and the test article was concluded to meet the requirements of ISO 10993-11, contains no pyrogens, is non-mutagenic based on the methods employed.

An exemplary material according to the invention is treated using low-temperature carburization which, in contrast with other treatment methods, minimizes the formation of carbides. U.S. Pat. No. 6,464,448 entitled "Low Temperature Case Hardening Process," the entire disclosure of which is incorporated herein by reference, describes low temperature carburization of a ferrous based material for industrial parts and assemblies. These processes were not previously applied to implant grade medical devices or implants perhaps because the presence of surface imperfections which, while not problematic in industrial settings, made the materials susceptible to corrosion when deployed in the body. The present application applies low-temperature carburization of steel or other materials to provide a corrosion resistant material sufficient for use in surgical instruments. That is, the exemplary system and method according to the invention adapts a novel technique of carburizing/nitriding an implant-grade, ferrite free material to form devices having increased corrosion resistance as compared to other materials known in the art in which corrosion may be caused, for example, in part by the binding of chromium to carbide instead of being available to form an oxide. Higher levels of molybdenum in the material according to the invention further increase the corrosion-resistance thereof. As those skilled in the art will understand, a combination of annealing and cold-working may be used to form any of the devices described herein. The resultant material includes a diffusion zone in which carbon has supersaturated the matrix in the form of an interstitial carbon. The effect of this supersaturation is improved hardness, wear resistance and corrosion resistance. The exemplary material of the invention is described in greater detail below.

As those skilled in the art will understand, there are three main cubic forms of iron: austenite (FCC), Martensite (BCT) and ferrite (BCC). Both Martensite and ferrite are magnetic, while austenite is not. Thus, conventional implant quality 316L stainless steel is intentionally balanced to be fully austenitic even in the as-cast condition to minimize or eliminate the interaction of the medical device with. MRI magnetic fields. This is done by balancing ferrite stabilizing elements with austenite stabilizing elements in such a way as to ensure that the as-cast balance is in the austenite region. It is well known that certain elements stabilize either austenite or ferrite. Since many of the ferrite stabilizing elements, such as molybdenum and chromium, also promote corrosion resistance, they must be balanced by increasing the austenite forming elements or the alloy will contain ferrite along with the austenite. Specification ranges may seem overly broad. However, when one balances the need to create certain phase balances with the need to maximize corrosion resistance while minimizing cost, it becomes evident that actual chemistries will vary in a much smaller range than the specifications imply. In conventional industrial versions of 316L, a certain amount of ferrite is purposely present in the alloy to improve welding characteristics of the alloy as ferrite is known to reduce hot cracking in welds. For the steelmaker, this provides a similar reduction of hot cracking during melting and casting, especially during continuous casting. The typical commercial 316L material is an alloy that contains a majority austenite with a small percentage of ferrite. This is true in the as-cast condition and also as finished wrought products such as bar, wire, sheet and plate.

On the other hand, implant quality 316L is chemically balanced so that no ferrite is present in the alloy. Although the chemical ranges given in specifications such as ASTM F 138 are capable of producing ferrite, the specifications require that the end product contain no ferrite. To accomplish this, producers balance the actual chemistry into the 100% austenite region. There are many methods for predicting the austenite-ferrite balance in stainless steels. Two of the most common are the Schaeffler and the WRC-1992 diagrams. In each of these techniques, a correlation has been made between the chrome equivalent, the nickel equivalent and the phase balance. The chrome and nickel equivalents relate the total amount of ferrite or austenite forming elements present to their stabilizing effect in relation to the base elements of chrome and nickel. Carburization is a diffusion controlled process wherein only a small region near an exterior surface layer of a device on the order of 20 μm -35 μm thick is carburized. If a ferrite grain remains present in this region, it will not be carburized forming an uncarburized area that will not be as corrosion resistant as the carburized layer. Corrosion tunneling effects can occur in these areas allowing corrosion to penetrate to the core of the item potentially resulting in catastrophic failure.

The exemplary material according to the invention utilizes implant quality 316L for carburizing as it does not contain any ferrite, thus mitigating the risk of the presence of ferrite particles disrupting the carburized layer. To show the propensity for formation of ferrite, the following were compared: (1) implant quality 316L received at Synthes that meets the requirements of ASTM F138, ASTM F 139 and ISO 5832-1. Sample size—1366 samples and (2) industrial quality 316L produced by a supplier to the requirements of ASTM A 276. —Samples size—3,556 samples. The average chemistry of each was plotted to determine the ferrite content using the Schaeffler and the WRC-1992 methods, as shown in the following tables:

| Industrial Quality 316L | | | |
|---|---|---|---|
| | N | Average | A 276 Limits |
| C | 3557 | 0.023467 | 0.08 max |
| Mn | 3558 | 1.460599 | 2.00 max |
| P | 3558 | 0.027386 | 0.045 max |
| S | 3557 | 0.022573 | 0.03 max |
| Si | 3558 | 0.577813 | 1.00 max |
| Cr | 3558 | 16.90085 | 16.0-18.0 |
| Ni | 3558 | 10.37691 | 10.0-14.0 |
| Mo | 3556 | 2.077068 | 2.00-3.00 |

| Implant Quality 316L | | | |
|---|---|---|---|
| | N | Average | ASTM F 138 Limits |
| C | 1366 | 0.017471 | 0.030 max |
| Mn | 1366 | 1.677483 | 2.00 max |
| P | 1366 | 0.017485 | 0.025 max |
| S | 1366 | 0.001069 | 0.010 max |
| Si | 1366 | 0.420132 | 0.75 max |
| Cr | 1366 | 17.46971 | 17.00-19.00 |
| Ni | 1366 | 14.46273 | 13.00-15.00 |
| Mo | 1366 | 2.771717 | 2.25-3.00 |
| N | 1366 | 0.073903 | 0.10 max |
| Cu | 1366 | 0.101012 | 0.50 max |
| Cr + 3.3Mo | 1366 | 26.6164 | 26.0 min |

Figures 11, 12:
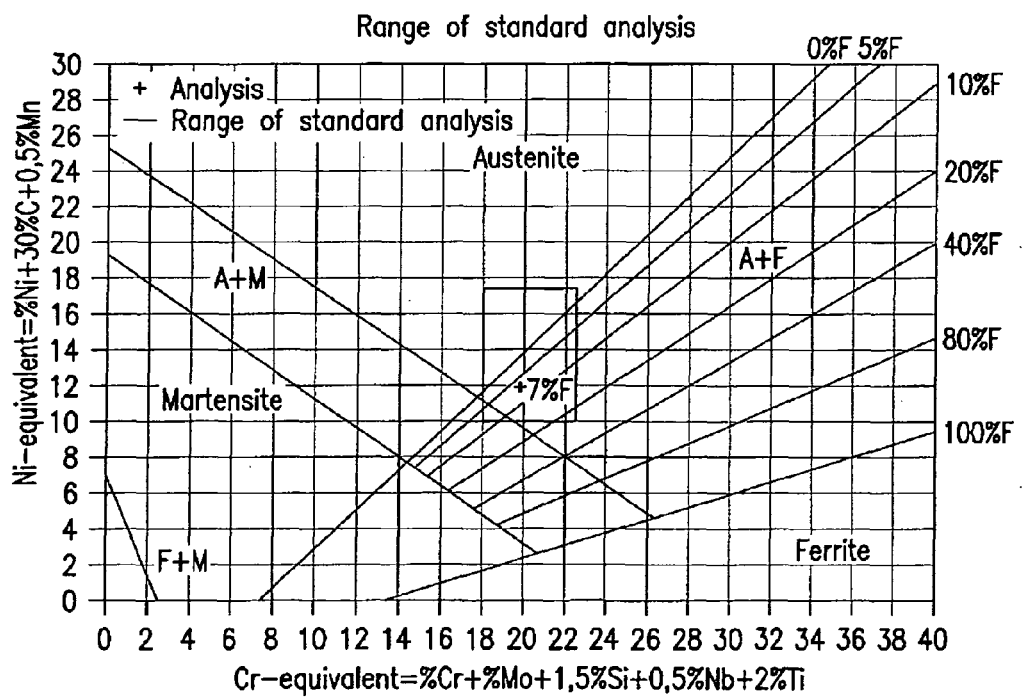
FIG. 11 shows a chart of conventional material compositions tested via a Schaeffler diagram for standard analysis.
FIG. 12 shows the Schaeffler diagram for the material of FIG. 11.
Figures 13, 14:
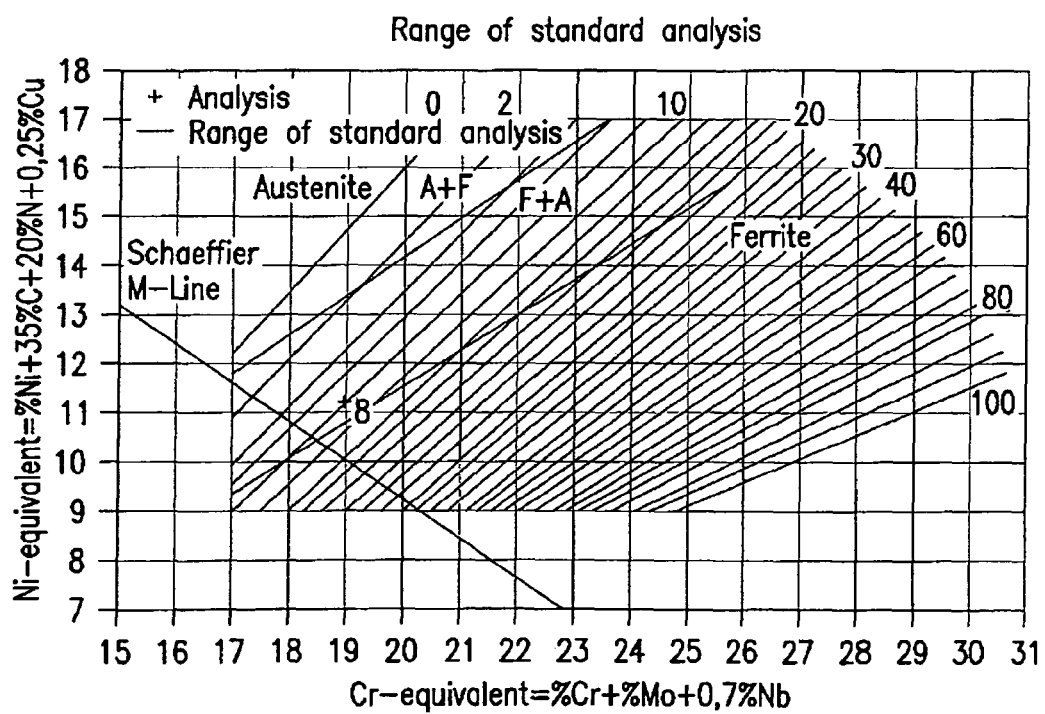
FIG. 13 shows a chart of conventional material compositions tested via a WRC-1992 diagram for standard analysis.
FIG. 14 shows the WRC-1992 diagram for the material of FIG. 13.
Figures 15, 16:
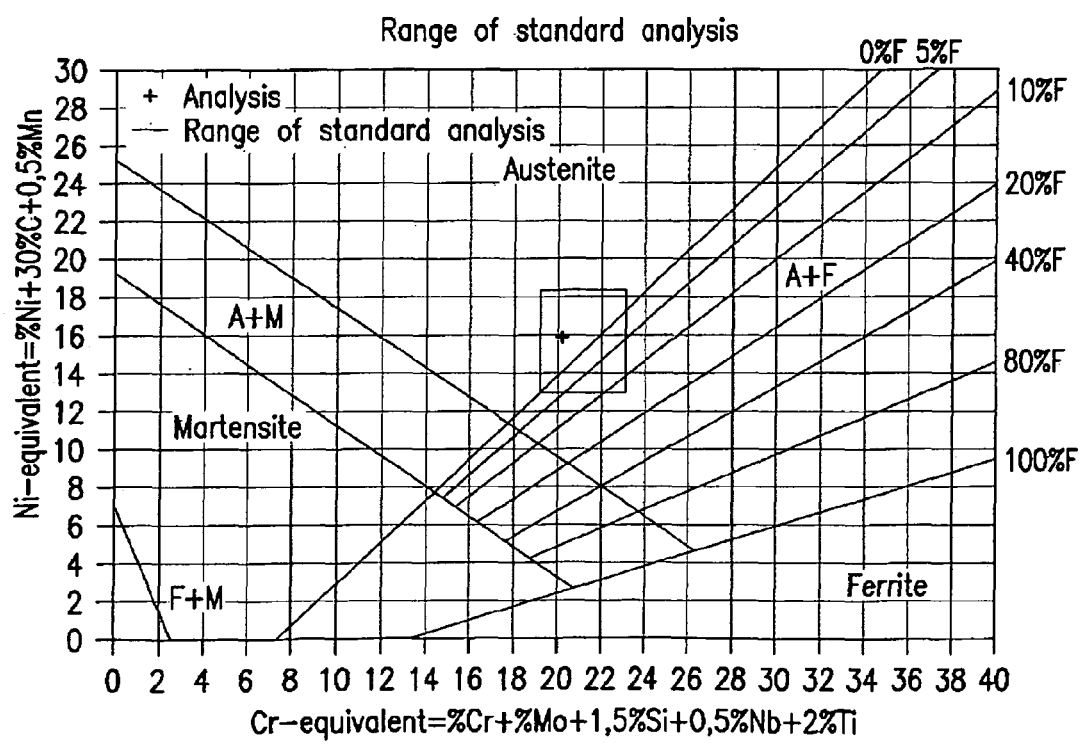
FIG. 15 shows a chart of an exemplary material composition according to the invention tested via a Schaeffler diagram for standard analysis.
FIG. 16 shows the Schaeffler diagram for the material of FIG. 15.
Figures 17, 18:
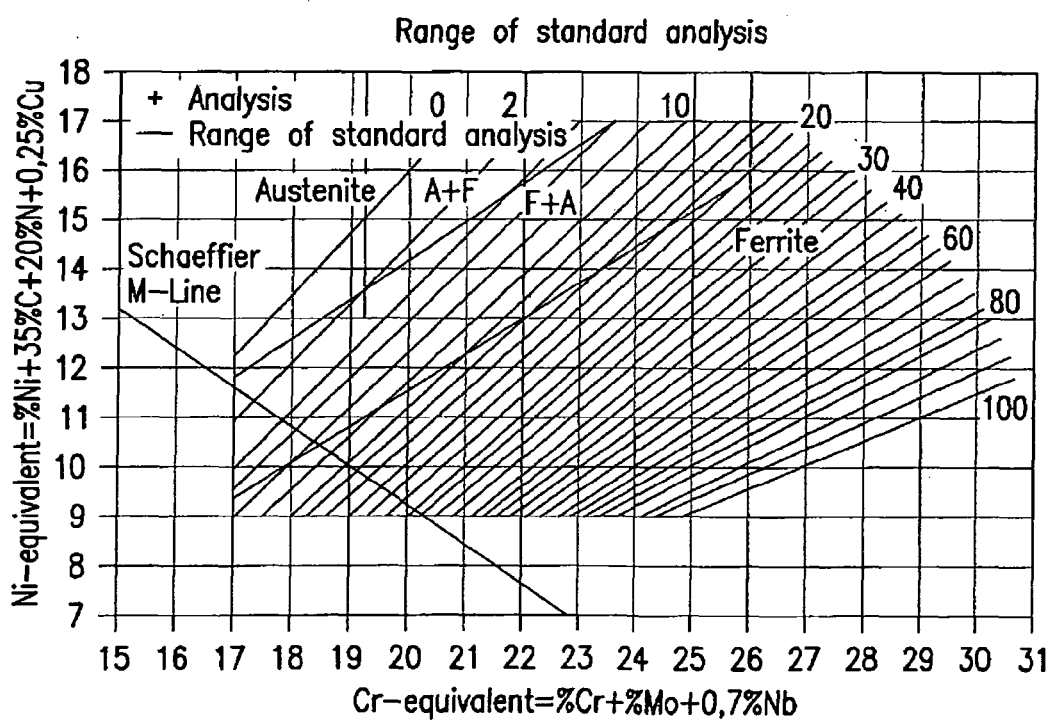
FIG. 17 shows a chart of the exemplary material composition according to the invention tested via a WRC-1992 diagram for standard analysis.
FIG. 18 shows the WRC-1992 diagram for the material of FIG. 17.

As depicted in FIGS. 11-18, the comparison of the above disclosed materials show that the implant quality 316L is balance into the 100% austenite region, while the industrial quality 316L is balanced at approximately 7-8% ferrite. Each of the techniques also shows the possible % ferrite band based on the specification ranges. Specifically, FIG. 12 provides information on the welding properties of various types of conventional industrial strength microstructures of FIG. 11 as a function of the alloying elements they contain. The chart of FIG. 12 corresponds to a Schaeffler diagram for a range of standard analysis for the following material compositions. FIG. 14 provides information on welding properties of the various types of conventional industrial strength microstructures of FIG. 13 as a function of the alloying elements they contain. The chart of FIG. 14 corresponds to a WRC-1992 diagram for a range of standard analysis for the following material compositions. FIGS. 15-18 provide the same data for the exemplary implant grade material according to the invention, wherein FIG. 16 corresponds to a Schaeffler diagram of the data of FIG. 15 and FIG. 18 corresponds to a WRC-1992 of the data of FIG. 17. In light of the above, it is evident that the exemplary material according to the invention provides an implant grade material that is balanced in a 100% austenite region, eliminating the ferrite commonly produced in conventional materials.

Although the exemplary construction depicted herein is directed to a bone fixation device 100 such as a bone screw, the inventive concept may be employed with any other bone fixation device/implant without deviating from the scope of the invention. Such bone fixation devices include, but are not limited to bone pins, buttress pins, bone plates, intramedullary nails, trochanteric nails, etc.

FIGS. 7-10 depict the exemplary bone fixation device 200 according to the invention. Although the device 200 shown is a bone plate, it is submitted that any other bone fixation device may be used without deviating from the scope of the invention (e.g., an intramedullary nail, etc.). The bone plate 200 may, for example, be a 4 5 mm broad variable angle compression plate including eight holes 202 extending through a body 204. Any or all of the holes 202 may be formed as variable angle combination holes comprising a first variable angle hole portion 206 and a second compression hole portion 208 open to the first hole portion. The first hole portion 206 may comprise a first relief cut 210 formed adjacent a first surface 203, a second cylindrical threaded portion 212 extending distally therefrom and a third relief cut 214 formed adjacent a second surface 205 configured to contact the bone in an operative configuration. The relief cut 210 may extend at an angle of approximately 15° relative to a longitudinal axis of the hole 202, although other angles may be used without deviating from the scope of the invention. The first hole portion 206 further comprises one or more slots 207 provided on an outer wall thereof, the slots 207 extending substantially perpendicular to a screw hole axis. As those skilled in the art will understand, the slots 207 interrupt the threads of the threaded portion 212 to provide multiple thread starts which aid in alignment of the threaded portion 212 with the bone screw 100. The second hole portion 208 may comprise a first tapered hole portion 216 and a second tapered hole portion 218 extending distally therefrom. It is noted that although the bone fixation device 200 is depicted with eight holes, any other number of holes may be used without deviating from the scope of the invention and these holes may include any variety of know bone screw mounting holes. The bone fixation device 200 may also comprise any number and combination of variable angle holes, single holes and combination holes without deviating from the scope of the invention. The second surface 205 may further comprise a plurality of undercuts 220 configured to reduce a contacting surface area between the bone fixation device 200 and the bone to, for example, reduce impairment of blood supply after implantation, as those skilled in the art will understand.

In an operative configuration, the bone screw 100 is inserted through the bone fixation device 200 and into the bone. As those skilled in the art will understand, a physician or other user may select a desired angle of insertion to conform to the requirements of a particular procedure. Multiple thread starts provided by the grooves 112 provided on the head 104 and the slots 207 provided in the hole 202 aid in alignment of the threads 110 of the head with the threaded portion 212 of the hole 202. As the bone screw 100 is screwed through the bone fixation device 200 and into the bone, the carburized or nitrided outer surface of the bone screw 100 minimizes burring of the threads 110. The increased rigidity of the bone screw 100 relative to the bone fixation device 200 also permits removal and reinsertion of the bone screw 100 into the bone (e.g., to correct a position thereof within the bone) without causing a burring thereof.

The exemplary carburized or nitrided outer surface according to the invention is not limited to the bone screw 100. In another embodiment, the carburized or nitrided outer surface and the ferrite-free construction may be applied to any conventional bone screw including, but not limited to, a variable angle bone screw, locking screw, compression screw or any other bone screw known in the art. The exemplary bone screw may be formed without any grooves 112 on the head 104. An outer profile of the head 104 may be one of tapered, rounded, spherical and cylindrical.

Figure 19:
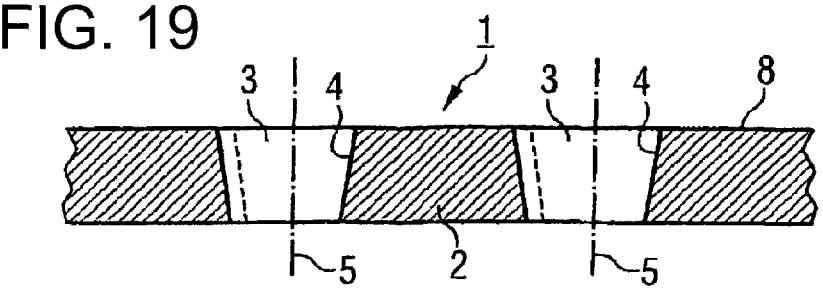
FIG. 19 shows a longitudinal section through a bone plate with tapered holes in the plate.
Figure 21:
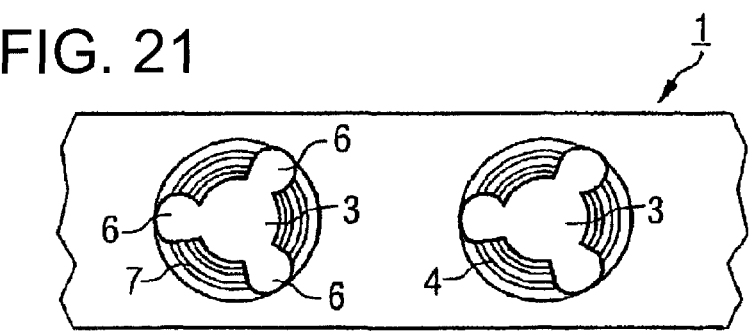
FIG. 21 shows a top view of a bone plate with three recesses in the internal jacket surface of the holes in the plate.

In one embodiment, the bone screw may be formed similar to the bone screw 10 disclosed in U.S. Pat. No. 8,343,196 entitled "Bone Plate", the entire disclosure of which is incorporated herein by reference. Specifically, as shown in FIGS. 19 and 21, a bone plate 1 has an underside 2 on a bone-contacting side thereof, an upper side 8 and a plurality of holes 3 in the plate connecting the underside 2 with the upper side 8, the holes having a central hole axis 5. The holes 3 in the plate have an internal jacket surface 4 that tapers towards the underside 2. Furthermore, the internal jacket surface 4 has three recesses 6 which extend radially away from the hole axis 5 of the hole at a uniform distance of 120 degrees from one another. Their peripheral expansion is approximately 40 degrees and they extend exclusively within the internal jacket surface 4. The recesses 6 extend tapered over the entire height of the bone plate 1 from the upper side 8 to the underside 2. In addition, the internal jacket surface 4 is provided with a three-dimensional structure 7 in the form of a thread.

Figure 22:
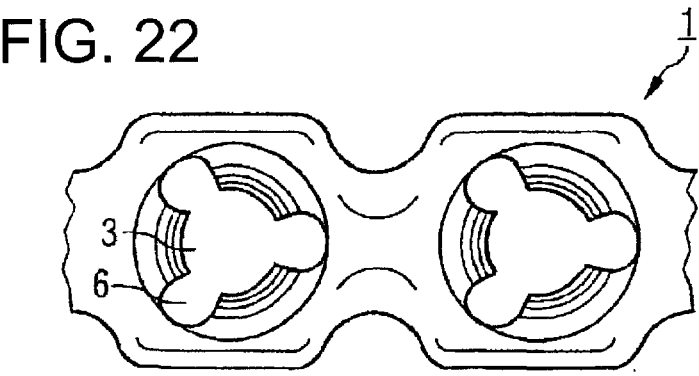
FIG. 22 shows a variation of the bone plate according to FIG. 21 with larger recesses in the internal jacket surface of the holes in the plate.

FIG. 22 illustrates a variation of the execution according to FIG. 21, wherein the recesses extend radially away from the axis of the hole past the internal jacket surface.

Figure 20:
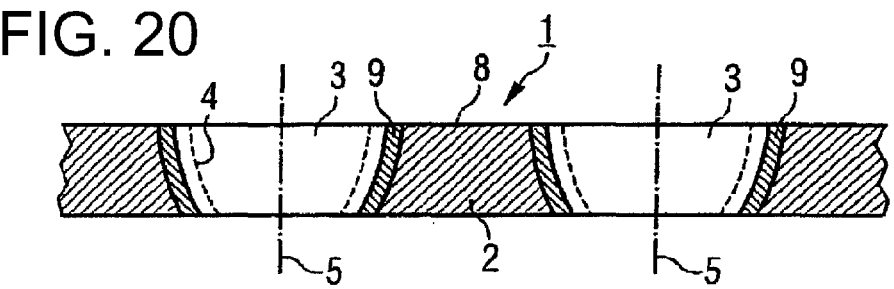
FIG. 20 shows a longitudinal section through a bone plate with spherical holes in the plate.
Figure 23:
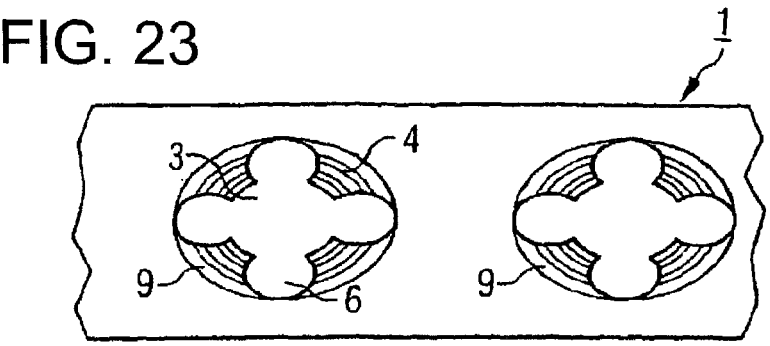
FIG. 23 shows a top view of a bone plate with thread inserts with four recesses in the internal jacket surface of the elliptic holes in the plate.

FIGS. 20 and 23 illustrate a further alternative embodiment, wherein the holes 3 in the plate are constructed as oblong holes. The bone plate is made basically from a plastic material (PEEK) with embedded metallic thread inserts 9 from titanium, forming the holes 3 in the plate. In the case of this embodiment the holes 3 in the plate have four recesses 6, which extend radially away from the axis 5 of the hole past the internal jacket surface 4. The internal jacket surface 4 is divided into four sections of the jacket surface. The recesses extend tapered over the entire height of the bone plate 1 from the upper side 8 to the underside 2. In addition, the internal jacket surface 4 is provided with a three-dimensional structure 7 in the form of a multi-start thread. As far as material is concerned, this embodiment may also be inverted, whereby the bone plate is basically made from metal (titanium) and the embedded therein thread inserts 9 are made from plastic material (PEEK), forming the holes 3 in the plate. The bone plate 1 may alternatively be formed of any other material known in the art exhibiting a hardness as described in greater detail with respect to earlier embodiments. The bone screws 10 may be formed of a ferrite-free biocompatible material having a carburized or nitrided outer surface, as also described in greater detail earlier.

Figure 24:
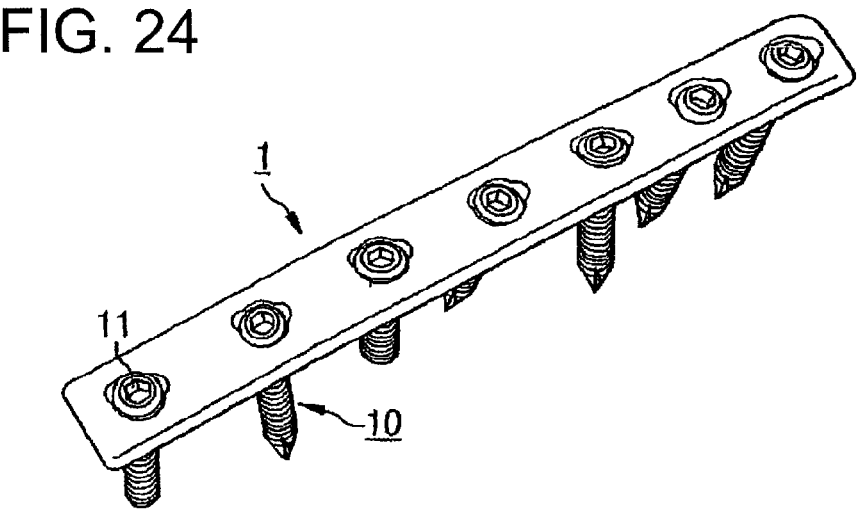
FIG. 24 shows a perspective view of a bone plate according to FIG. 19 from above with the bone screws inserted.
Figure 25:
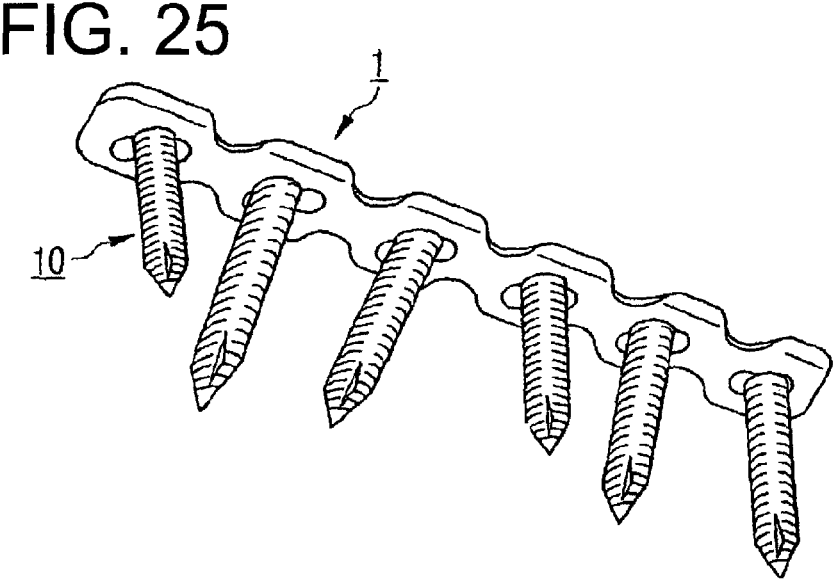
FIG. 25 shows a perspective view of a bone plate according to FIG. 19 from below with the bone screws inserted.

FIG. 24 illustrates the bone plate according to FIG. 19, with bone screws 10 inserted from above, the head portions 11 of which are spherical. FIG. 25 shows the same bone plate 1 from below.

Figure 26:
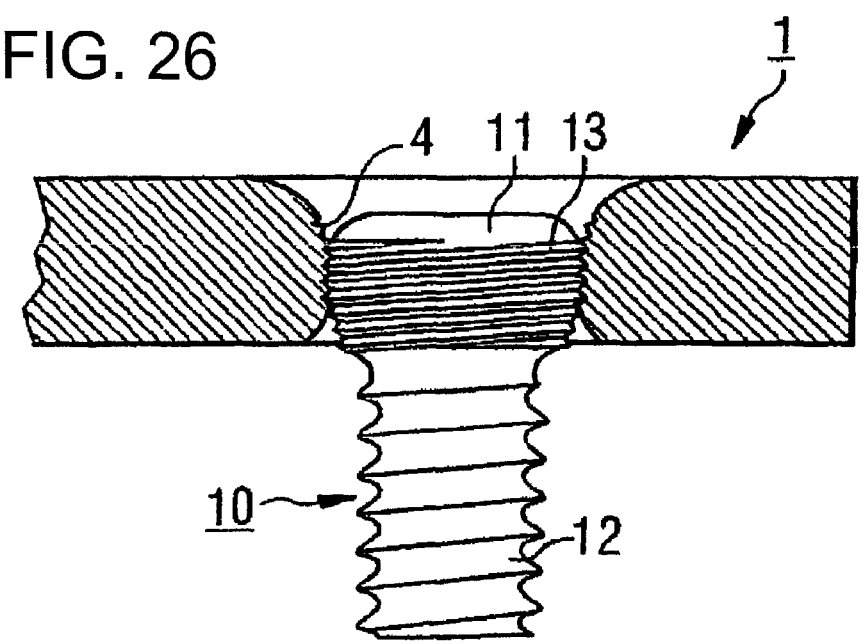
FIG. 26 shows a longitudinal section through a bone plate with a bone screw inserted without angular misalignment.
Figure 27:
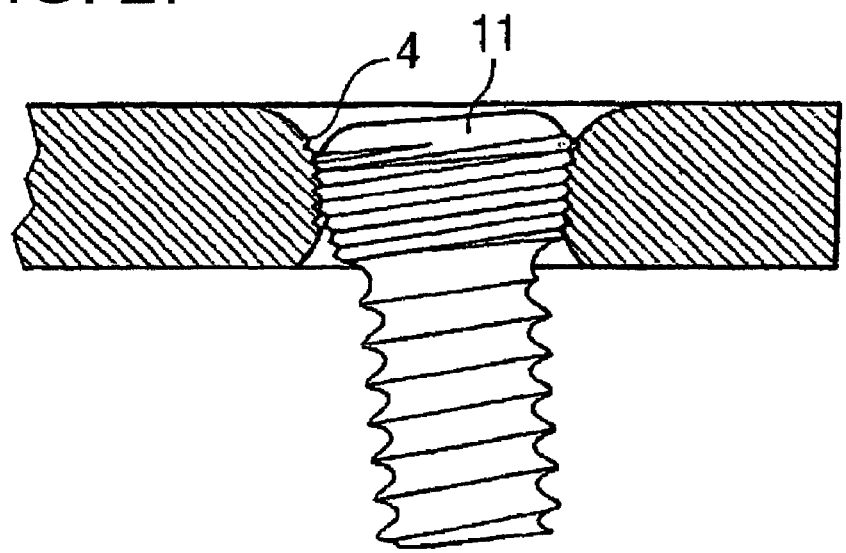
FIG. 27 shows a longitudinal section through a bone plate with a bone screw inserted with angular misalignment.

In FIG. 26, a bone plate 1 is illustrated with bone screws 10 inserted therein without angular misalignment. The internal jacket surface 4 of the hole of the bone plate 1 and the head portion 11 of the bone screw 10 have matching threads 13. FIG. 27 illustrates the same variation as FIG. 26, while the bone screw 10 is angularly misaligned.

Figure 28:
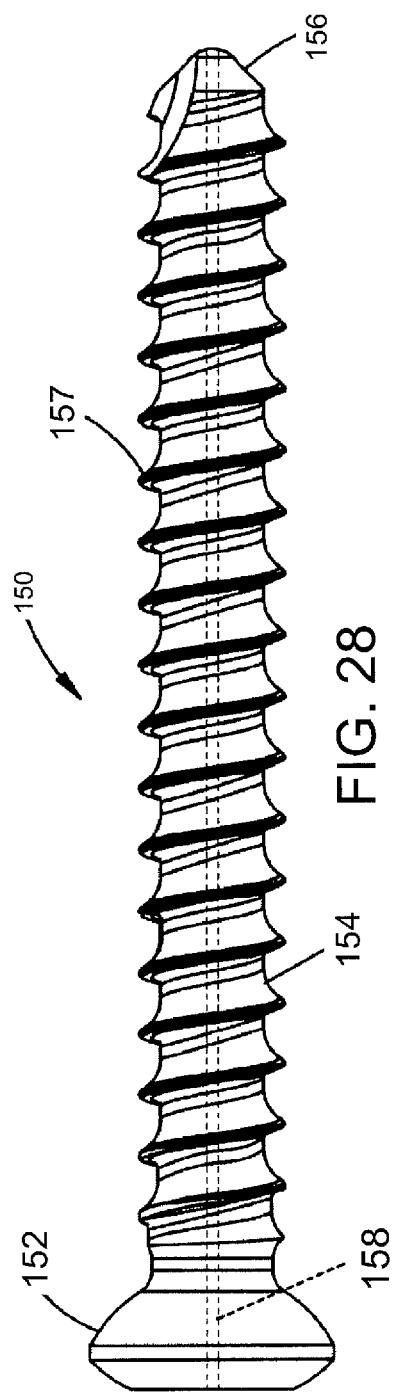
FIG. 28 is an elevation view of a non-locking bone screw.

In another embodiment, the bone screw may be similar to the bone screw 100, 200, 300, 500, 600, 702, 1360, 14100, 14200, 31200 of U.S Publication No. 2008/0140130, the disclosure of which is also incorporated herein. Specifically, FIG. 28 shows a typical non-locking bone screw 150, also known as a cortex screw. Generally, any surgical bone screw having a non-threaded head 152 with a generally smooth surface and of an appropriate size and geometry for a selected plate hole can be formed with the exemplary material and carburized or nitrided outer surface according to the invention. The shape of head 152 may be, for example, conically tapered, straight-sided, spherical, hemispherical, etc. Non-locking screw 150 has a shaft 154 that is at least partially threaded for attachment to bone. The length of shaft 154 and the thread configuration (e.g., pitch, profile, etc.) of shaft thread 157 can vary depending on the application. As is known in the art, tip 156 and shaft threads 157 may be self-tapping and/or self-drilling to facilitate implantation into bone. Head 152 and shaft 154 may also have a cannula 158 for receiving a guide wire to aid in proper placement.

Figure 29:
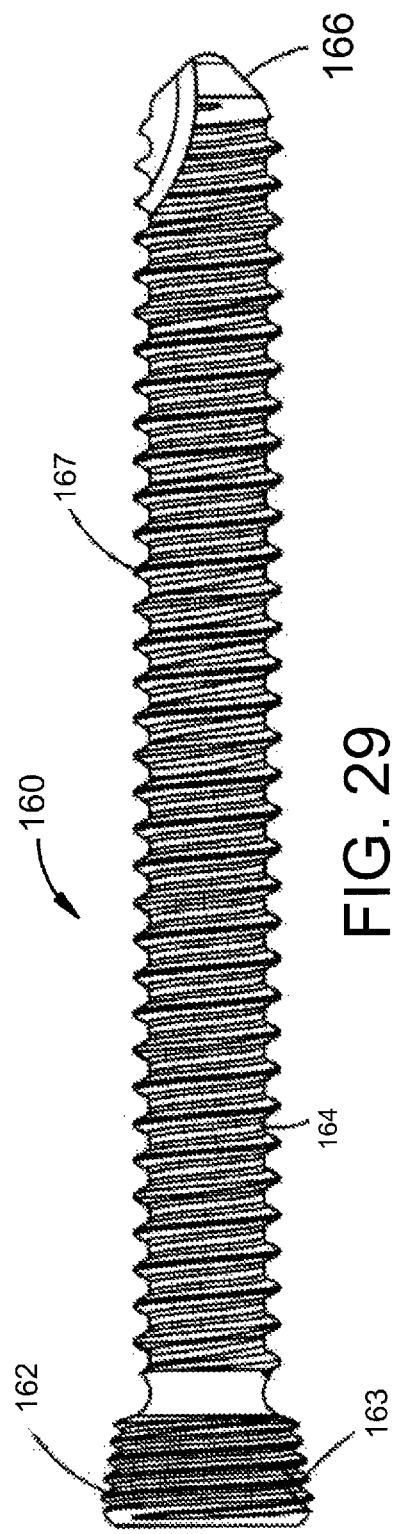
FIG. 29 is an elevation view of a locking bone screw.

FIG. 29 shows a typical locking screw 160. Generally, any surgical bone screw having a threaded head 162 can be used with the invention provided that head 162 is of an appropriate size and geometry for a selected plate hole and that threads 163 mate with the columns of thread segments in the plate hole. The shape of head 162 is typically conically tapered, but also may be, for example, straight-sided. Locking screw 160 has a shaft 164 that is at least partially threaded for attachment to bone. The length of shaft 164 and the thread configuration (e.g. pitch, profile, etc.) of shaft thread 167 can vary depending on the application. As is known in the art, tip 166 and shaft threads 167 may be self-tapping and/or self-drilling to facilitate implantation into bone. Head 162 and shaft 164 may also be cannular for receiving a guide wire to aid in proper placement.

Figure 30:
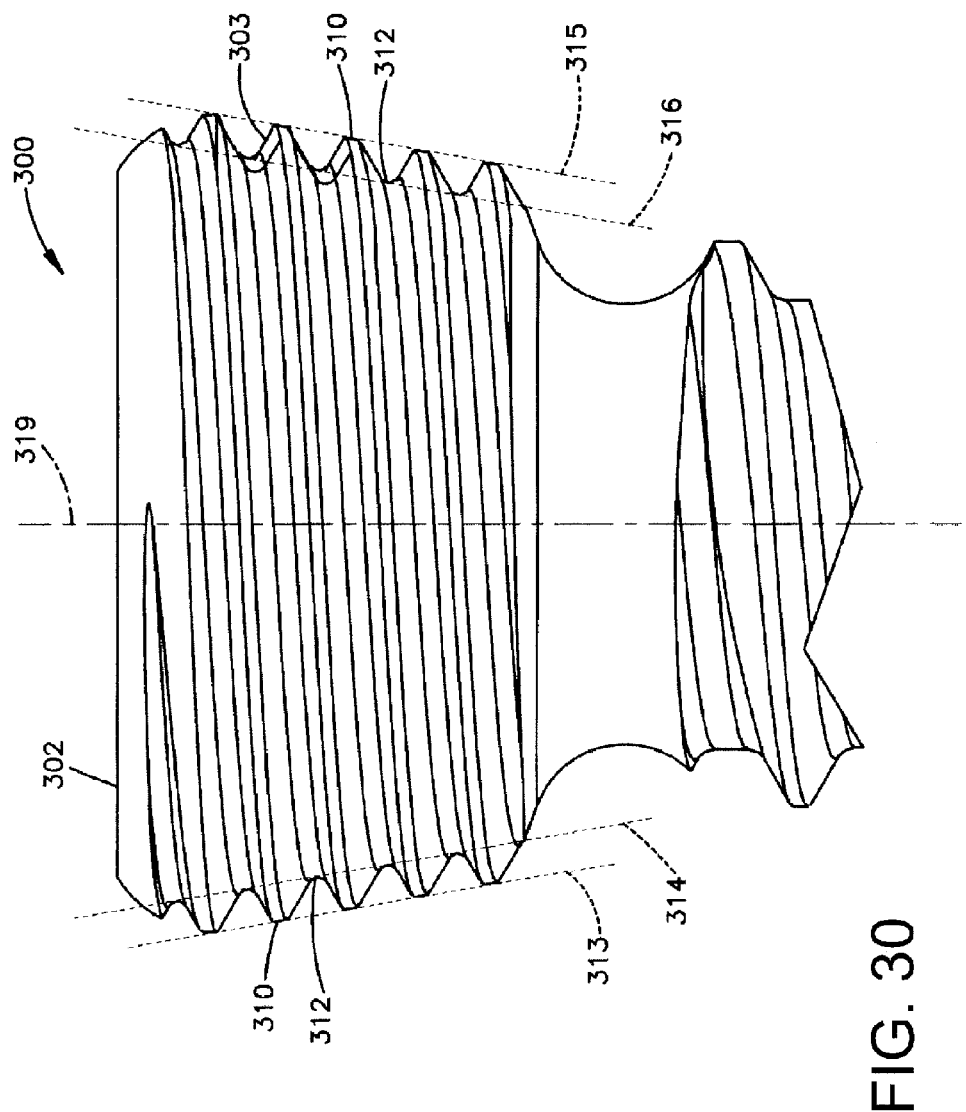
FIG. 30 is an elevation view of the head of a locking bone screw.

FIGS. 30 and 31 show head 302 of a typical locking screw 300. The profile of thread 303 on head 302 includes thread peaks 310 and troughs 312 connected to each other by flanks 311, two adjoining flanks 311 forming a thread angle 317, as shown in FIG. 32. Head 302, which is conically shaped as is usual on known locking screws, is typically oriented such that thread peaks 310 lie on a straight line, such as lines 313 or 315, and thread troughs 312 lie on another straight line, such as lines 314 or 316, wherein the pairs of lines (313, 314) and (315, 316) are parallel to each other. Furthermore, the thread profile lines of each thread peak 310 and each thread trough 312 extend parallel to each other and perpendicular or normal to the central axis 319 of the screw, as represented by trough profile lines 318*a-e* shown in FIG. 31. Profile lines 318*a-e* are formed by extending the longitudinal axis 301 of a cutting bit 305 of a thread cutter as the cutting bit contacts the outer surface of head 302 to cut thread 303. A typical locking screw also has a constant thread pitch (the distance from peak to peak, trough to trough, or profile line to profile line) as measured along the central axis (e.g., 319).

A variable-angle locking screw according to the invention has a screwhead that is at least partially spherical. The spherically-shaped portion of the head has a thread on an outer surface thereof which is preferably a double lead thread. The thread has a profile that follows the arc-shaped (i.e., non-linear) radius of curvature of the spherically-shaped portion of the head. Note that the thread pitch is constant as measured along the radius of curvature, but varies from narrow-to-wide-to-narrow as measured along the central axis of the screw from one end (e.g. the top) of the spherically-shaped portion of the head to the other end (e.g. the bottom) (see, e.g. FIGS. 57-60 and the description thereof further below). This thread profile allows the variable-angle locking screw to engage a bone plate hole of the invention at a selectable angle within a range of angles while advantageously maintaining the same degree of contact with the bone plate regardless of the angle chosen. That is, the angle of the screw with respect to the central axis of the bone plate hole within the permissible range of angles does not affect the engagement of the screwhead thread with respect to the inner surface of the plate hole. A tight lock is advantageously obtained between the screw and the bone plate regardless of the angle (within the range of angles) at which the screw is inserted into the bone plate hole, because the threads on the spherically-shaped portion of the screwhead engage the columns of thread segments in precisely the same manner, ensuring a good fit.

Figure 35:
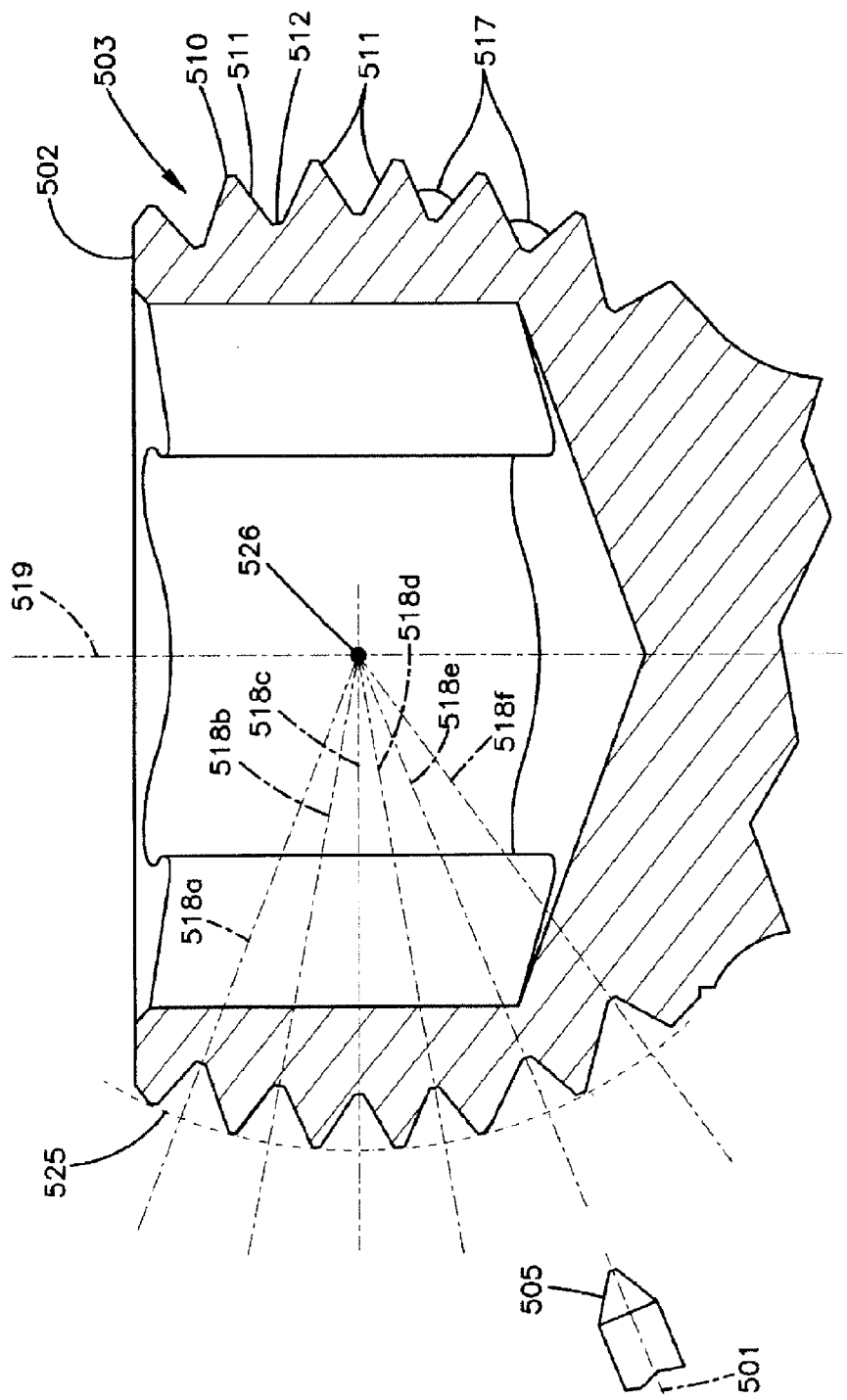
FIG. 35 is a cross-sectional view of the head of the variable-angle locking screw of FIG. 33.

FIGS. 33-35 show an embodiment of a variable-angle locking screw according to the invention. Variable-angle locking screw 500 has a partially-spherical head 502 and a shaft 504. Head 502 has a thread 503, and shaft 504 has a thread 507. Head 502 preferably has a recess 509 for receiving a tool to drive and extract the screw into and out of bone and into and out of a bone plate hole. Preferably, tip 506 and shaft thread 507 are self-tapping and/or self-drilling to facilitate implantation into bone. Head 502 and shaft 504 may be cannular for receiving a guide wire to aid in proper placement. FIGS. 34 and 35 show the profile of thread 503, which advantageously follows the radius of curvature 525. In one embodiment, the radius is about 2 mm. Respective peaks 510 and troughs 512 of thread 503 as seen in profile are preferably separated by equal angular increments. Peaks 510 and troughs 512 are connected by flanks 511 at thread angles 517, which in this embodiment, are preferably about 60 degrees. The thread profile lines 518a-f extend through troughs 512 and result in a series of lines that intersect the center 526 of the radius of curvature 525. Profile lines 518a-f are formed by extending the longitudinal axis 501 of a cutting bit 505 of a thread cutter as the cutting bit contacts the outer spherical surface of head 502 to cut thread 503. In this embodiment, cutting bit 505 is always normal to the outer spherical surface of head 502 as thread 503 is cut. Also in this embodiment, the radius of curvature is such that the radius center 526 lies on the central axis 519 of screw 500. Depending on the length of the radius and the dimensions of the screw, center 526 may or may not lie on the central axis of the screw. Moreover, as the radius increases while the dimensions of the screw remain constant, the radius center will move outside the screwhead, as shown, for example, in FIG. 36.

Figure 36:
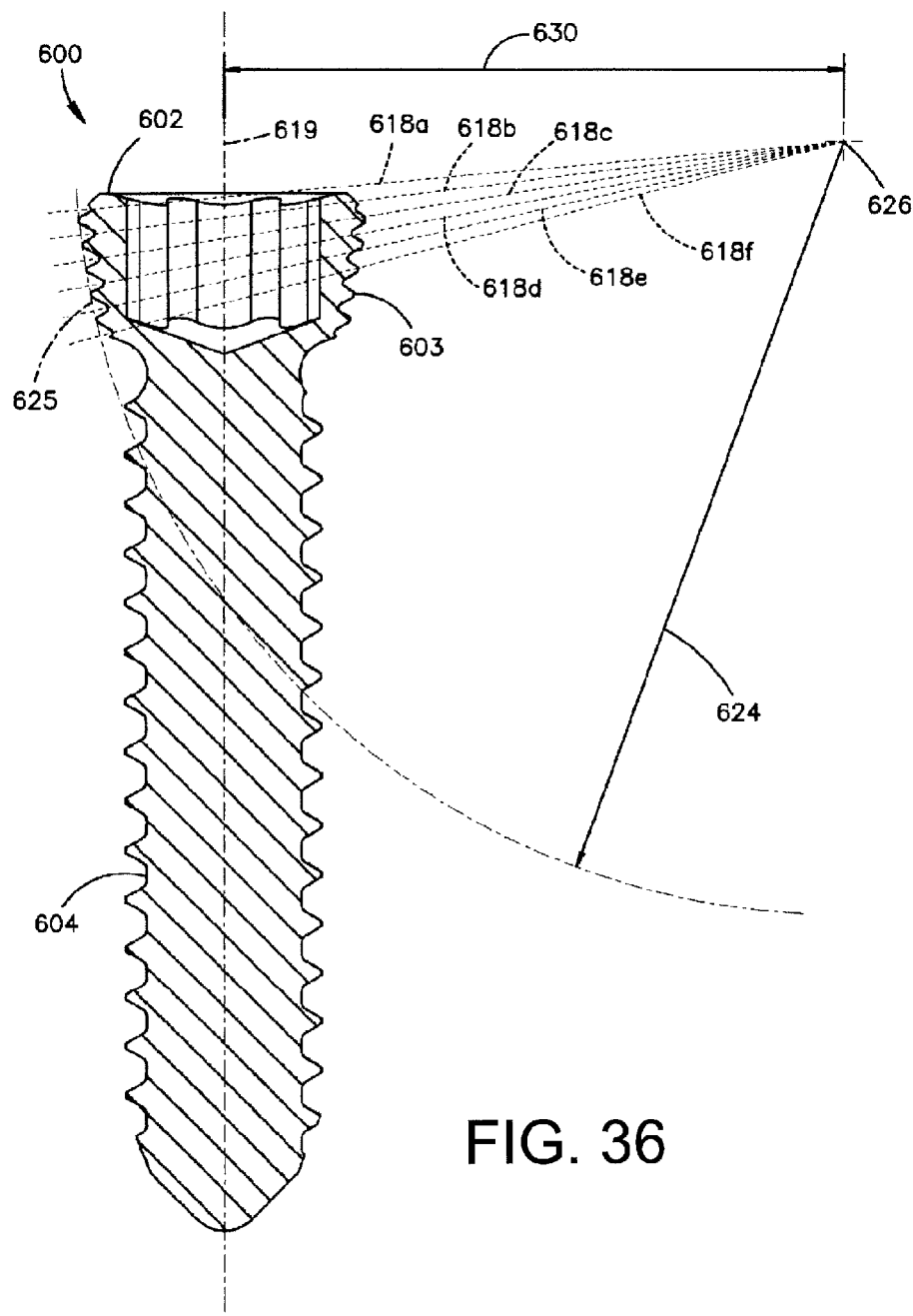
FIG. 36 is a cross-sectional view of another embodiment of a variable-angle locking screw according to the invention.

FIG. 36 shows another embodiment of a variable-angle locking screw of invention. In this embodiment, screwhead 602 of variable-angle locking screw 600 has a larger radius of curvature 625 than screw 500. This results in trough profile lines 618a-f intersecting radius of curvature center 626, which is a distance 630 (measured perpendicularly) from central axis 619 of screw 600. If, for example, radius 624 is 10 mm, distance 630 may be about 8.2 mm for a 2.4 mm screw (the 2.4 mm refers to the major diameter of shaft 604). Note, however, that as the radius of curvature increases, the screwhead becomes less and less spherical in shape, causing the thread profile to become more and more aligned with a straight line (such as, e.g., lines 313-316) as in known locking screwheads.

Figure 37:
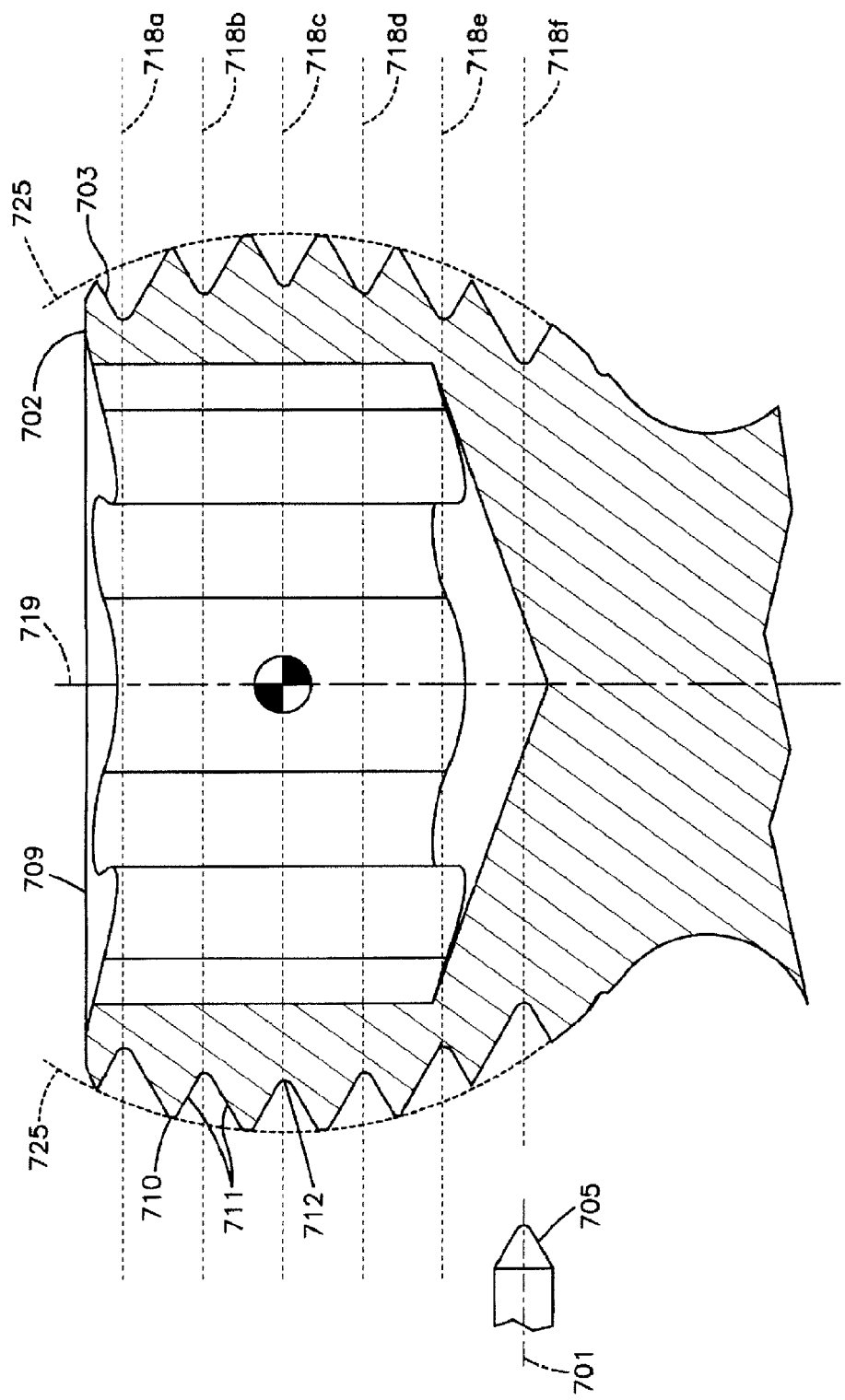
FIG. 37 is a cross-sectional view of a still another embodiment of a variable-angle locking screwhead according to the invention.

FIG. 37 shows still another embodiment of a variable-angle locking screwhead in accordance with the invention. Screwhead 702 has a central axis 719, thread 703, and a recess 709 for receiving a driving/extracting tool. As in previous embodiments, the profile of thread 703 advantageously follows the arc-shaped (i.e., non-linear) radius of curvature 725 and includes thread peaks 710, troughs 712, and flanks 711. However, unlike previous embodiments, the thread profile lines do not intersect the center of the radius of curvature. Instead, the thread profile lines, represented by trough profile lines 718a-f, extend parallel to each other and perpendicular to central axis 719. These lines extend in this manner because of the way in which cutting bit 705 of a thread cutter contacts the outer spherical surface of head 702 to cut thread 703, lines 718a-f representing extensions of longitudinal axis 701 of cutting bit 705. Functionally, this difference results in a less ideal screwhead/hole thread engagement. However, screwhead 702 is currently easier to fabricate than screwhead 502.

Figure 39:
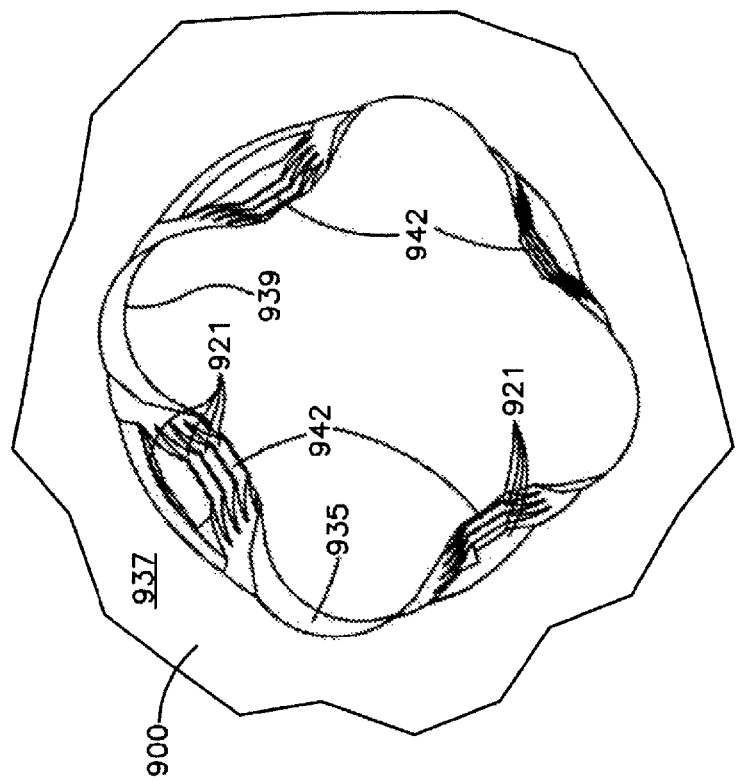
FIG. 39 is a second perspective view of an embodiment of the bone plate hole of FIG. 38.
Figure 38:
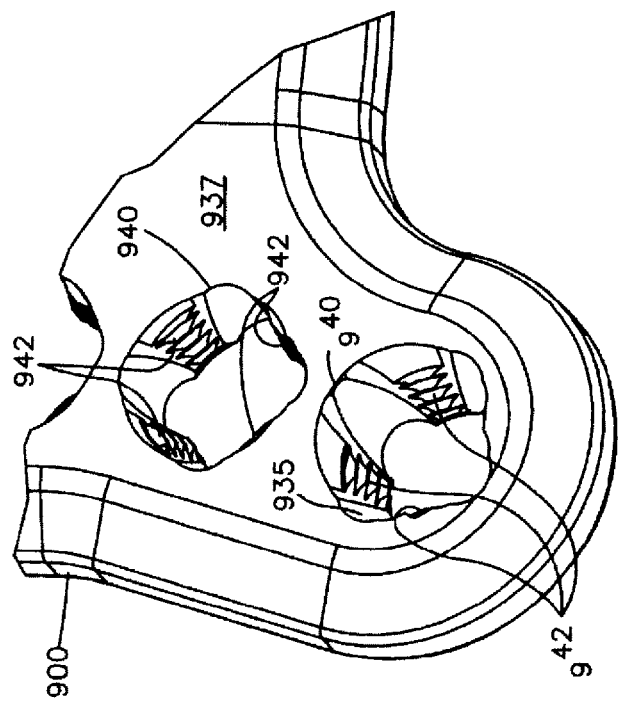
FIG. 38 is a first perspective view of an embodiment of a bone plate hole according to the invention.
Figure 40:
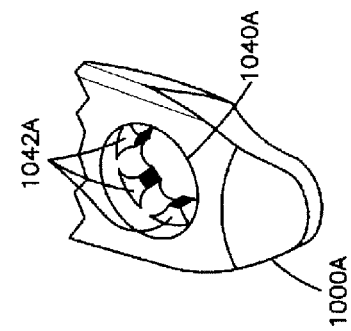
FIG. 40 is a top view of a bone plate hole according to another embodiment of the invention.
Figure 43:
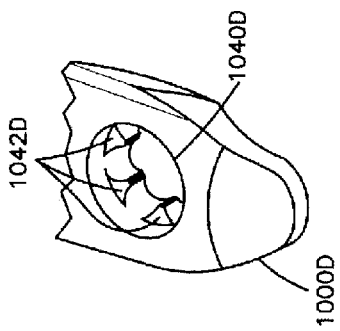
FIG. 43 is a top view of a bone plate hole according to yet another embodiment of the invention.
Figure 41:
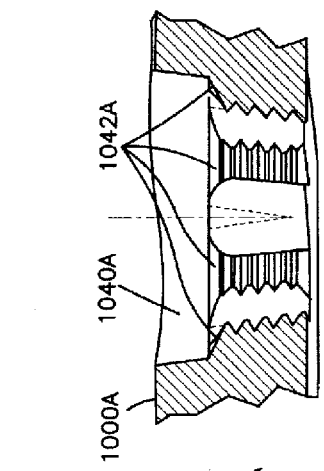
FIG. 41 is a cross-sectional view of the bone plate hole of FIG. 40.
Figure 44:
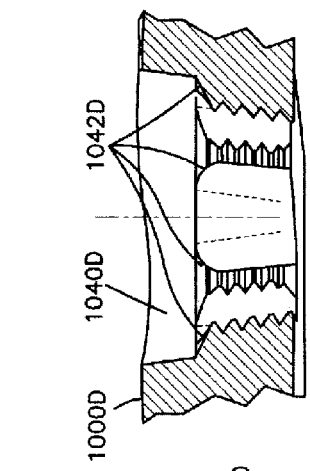
FIG. 44 is a cross-sectional view of the bone plate hole of FIG. 43.

FIGS. 38 and 39 show bone plate 900 having bone plate holes 940 in accordance with the invention. Instead of a helical thread around the inner surface 935 of the plate holes as in conventional locking screw bone plate holes, bone plate holes of the invention have discrete, vertical columns 942 of preferably thread segments arranged around the inner surface of the hole. The thread segment columns, if expanded to join each other (i.e. if extended completely around inner surface 935), would form a helical thread. The columns extend in a direction from upper surface 937 to lower surface 939 and are spaced preferably equidistantly apart around the inner surface of the hole. The number of thread segments 921 per column can vary depending on the surgical application and the dimensions of the bone plate and bone screw (e.g., plate thickness and thread pitch). However, each column should have at least two thread segments and preferably more to ensure a fixed angular relationship between the screw and the plate.

Note that instead of thread segments, columns 942 alternatively may have a plurality of teeth formed thereon. The columns of teeth, if expanded to join each other (i.e., if extended completely around inner surface 935), will not form a helical thread, but a series of concentric ridges and grooves perpendicular to the central axis of the bone plate hole. While such columns of teeth can also receive non-locking, locking, and variable-angle locking bone screws, the engagement of the teeth with the screwhead threads of the locking and variable-angle locking bone screws is less ideal than the engagement of thread segments with the screwhead threads of the locking and variable-angle locking bone screws.

Bone plate holes of the invention preferably have four columns 942 of thread segments, as shown in FIGS. 38 and 39. However, bone plate holes of the invention alternatively may have other numbers of columns of thread segments.

Figure 42:
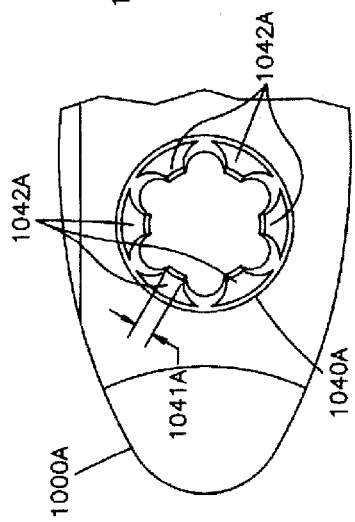
FIG. 42 is a perspective view of the bone plate hole of FIG. 40.
Figure 45:
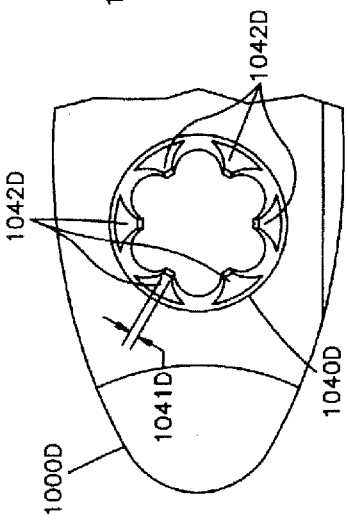
FIG. 45 is a perspective view of the bone plate hole of FIG. 43.

For example, as illustrated in the two embodiments of FIGS. 40-42 and 43-45, respectively, bone plate holes 1040A and 1040D of respective bone plates 1000A and 1000D each have six columns of thread segments (note that because of the perspective shown, only three columns are visible in FIGS. 42 and 45). The difference between thread segment columns 1042A and thread segment columns 1042D is that the column width 1041A of thread segments 1042A is about twice that of column width 1041D of thread segments 1042D. In one exemplary embodiment, 3 to 6 thread columns may be provided. It is noted, however, that any number of thread columns may be used without deviating from the scope of the invention.

Figure 46:
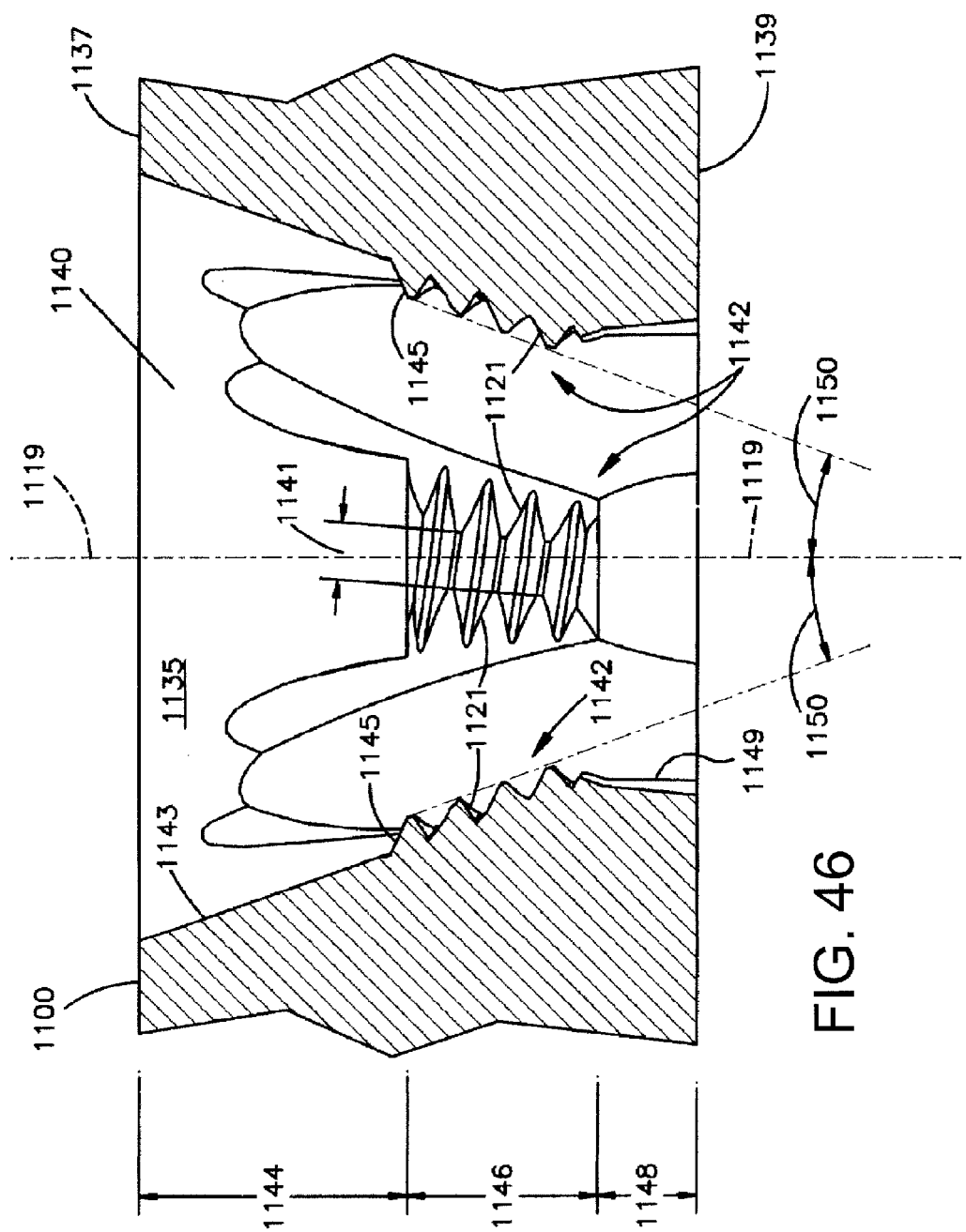
FIG. 46 is a cross-sectional view of a bone plate hole according to yet another embodiment of the invention.

FIG. 46 shows a cross-section of a bone plate hole according to the invention. Bone plate hole 1140 is formed in and extends completely through a bone plate 1100 from an upper surface 1137 to a lower bone-engaging surface 1139. Hole 1040 has an inner surface 1135 comprising a top portion 1144, a middle portion 1146, and a bottom portion 1148. Top portion 1144 extends from upper surface 1137 to middle portion 1146. Middle portion 1146 extends from top portion 1144 to bottom portion 1148 and preferably has the smallest diameter of the hole. And bottom portion 1148 extends from middle portion 1146 to lower surface 1139. Top portion 1144 is unthreaded, has a preferably smooth inner surface 1143, and is preferably conically tapered inward toward the lower surface. Bone plate hole 1140 has a shoulder 1145 at the intersection of top portion 1144 and middle portion 1146 (which is the top of the first thread segment in each column). Shoulder 1145 may serve as a stop for the screwhead of a non-locking bone screw inserted through hole 1140 and, in one embodiment, is angled such that it forms an angle of about 60 degrees with the central axis of the hole. Note that inner surface 1143 or upper surface 1137 may serve as a stop for the screwhead of a non-locking bone screw depending on the size and shape of the head. Bottom portion 1148 also has a preferably smooth inner surface 1149 and is preferably tapered inward toward the upper surface in the form of an undercut sphere. In one embodiment of the invention, the radius of the undercut sphere is about 1.75 mm. For a bone plate thickness of about 2 mm, for example, the top portion may extend about 1 mm and the middle and bottom portions each may extend about 0.5 mm.

In this embodiment, middle portion 1146 of bone plate hole 1140 has four discrete columns of thread segments 1142 on inner surface 1135. Each column 1142 is preferably inclined inward toward lower surface 1139 at an angle 1150 measured with respect to the central axis 1119. In one embodiment, angle 1150 is preferably about 15 degrees. Each column 1142 also preferably has four or five thread segments 1121. Other embodiments may have more or less thread segments as described above. For a bone plate hole accommodating a 2.4 mm variable-angle locking screw, the column width 1141 of each thread segment is preferably about 0.35 mm. Other embodiments may have other column widths, depending on the application.

Figure 47:
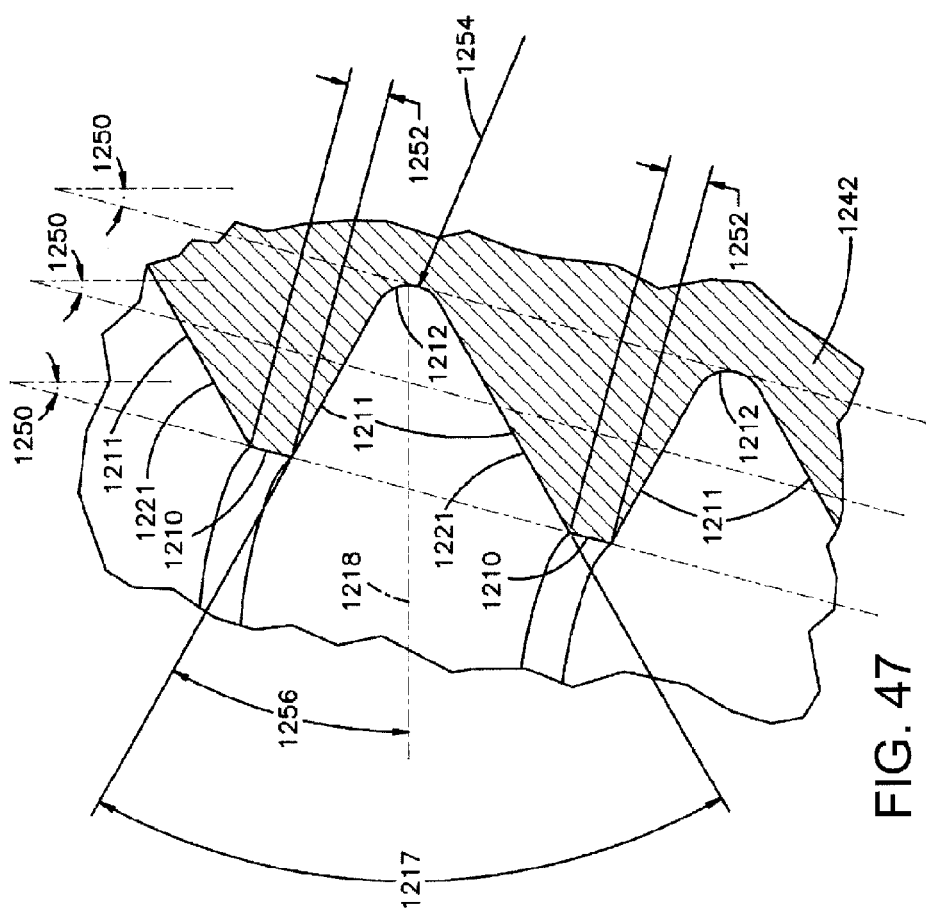
FIG. 47 is an enlarged, partial cross-sectional profile view of a column of thread segments of the bone plate hole of FIG. 46.

FIG. 47 shows a cross-sectional profile of a portion of a column 1242 of thread segments 1221. (Note that a cross-sectional profile of an alternative column of teeth, as described above, appears the same as the thread segments.) In FIG. 47, two of the five thread segments 1221 of column 1242 are shown. Column 1242 of thread segments is preferably inclined toward the lower surface of the bone plate at angle 1250. In one embodiment, angle 1250 is about 15 degrees. As seen in profile, column 1242 of thread segments 1221 includes peaks (or crests) 1210 and troughs (or roots) 1212 connected to each other by flanks 1211 at thread angles 1217. Peaks 1210 preferably have a length 1252, which in one embodiment is about 0.04 mm. Troughs 1212 preferably have a radius 1254, which in one embodiment is about 0.03 mm. Angle 1217 is preferably about 60 degrees, and the bisection of troughs 1212, as represented by trough profile line 1218, occurs at an angle 1256 of preferably about 30 degrees as measured from a flank 1211. Other embodiments of bone plate hole thread-segment columns alternatively may have other values of column incline angle, peak lengths, trough radiuses, thread angles, and bisection angles (which are a function of thread angle).

Figure 48:
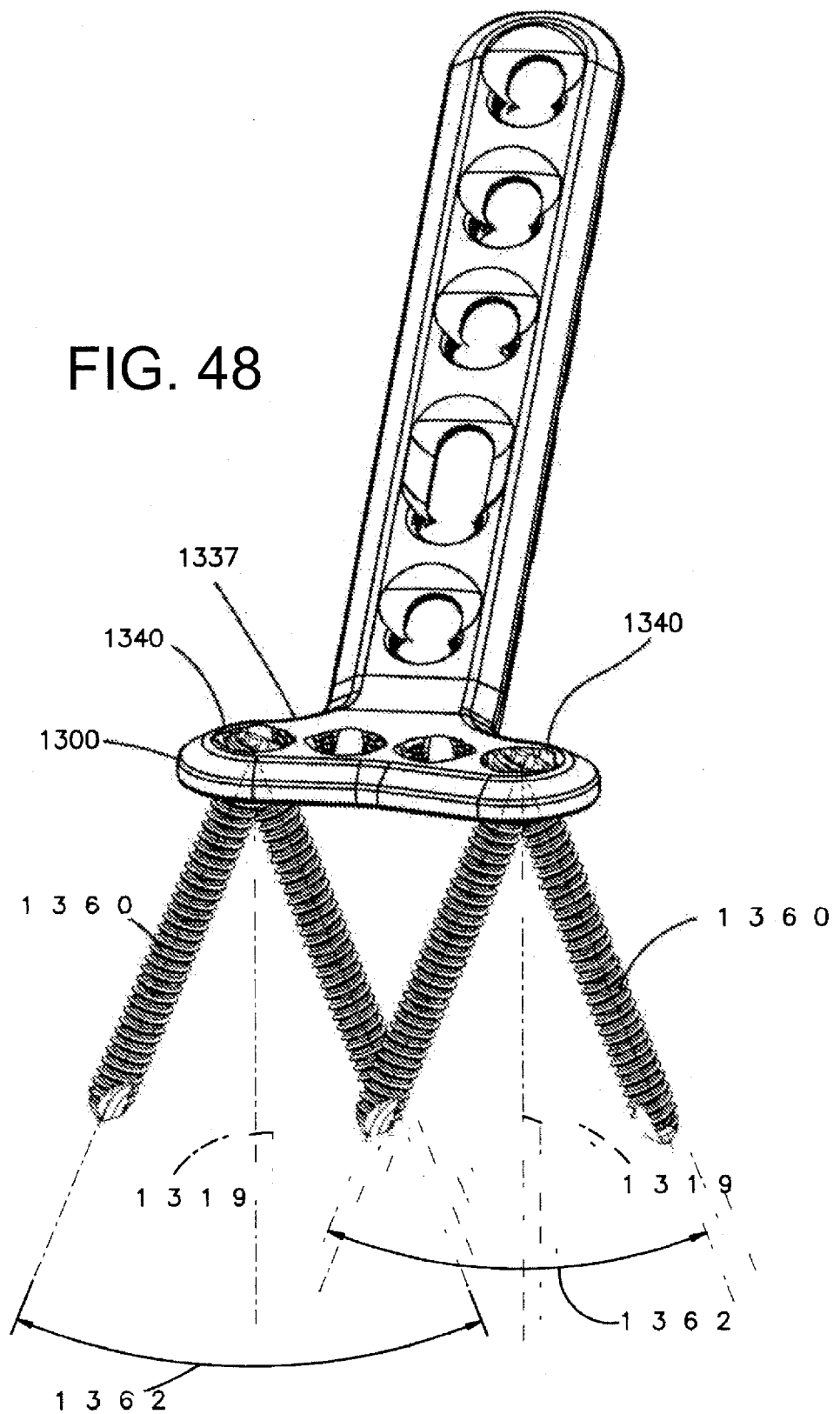
FIG. 48 is a perspective view of an embodiment of a bone plate system the range of selectable angles of a variable-angle locking screw according to the invention.
Figure 49:
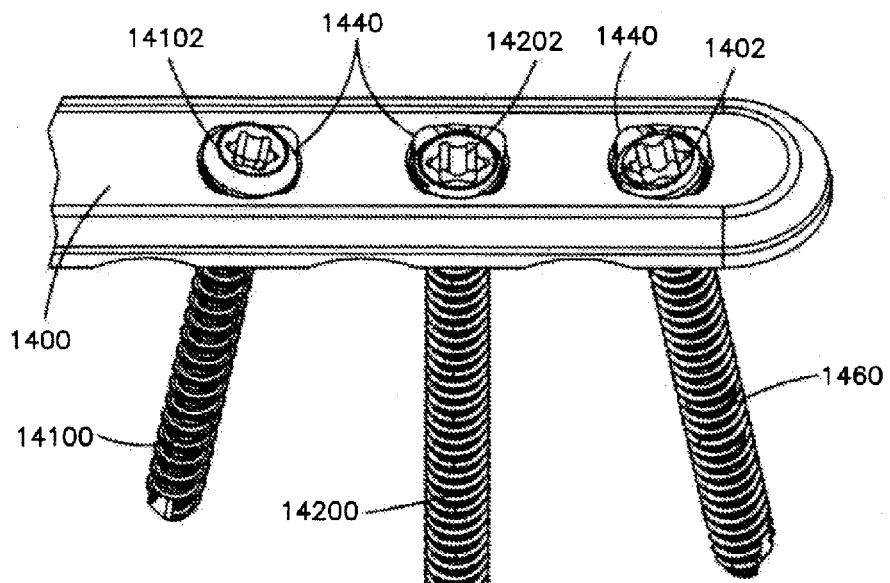
FIG. 49 is a perspective view of an embodiment of a bone plate system showing non-locking, locking, and variable-angle screws used with a bone plate according to the invention.

Advantageously, variable-angle locking bone screws of the invention can be driven into bone and secured to the bone plate at a selectable angle within a range of selectable angles. FIG. 48 shows an embodiment of the invention in which bone plate 1300 has bone plates holes 1340 constructed in accordance with the invention. Each hole 1340 can advantageously receive a variable-angle locking screw 1360, also constructed in accordance with the invention, at a selectable angle in any direction within a range of angles. The range of angles forms a cone having an angle 1362, which in this embodiment is about 30 degrees. In other words, variable-angle locking screw 1360 can be inserted into a hole 1340 and secured to bone plate 1300 at a selectable angle ranging from 0 degrees to 15 degrees in any direction with respect to central axis 1319 of bone plate 1340.

FIGS. 49-56 show an advantageous feature of a bone plate hole constructed in accordance with the invention. Bone plate 1400 has at least three bone plate holes 1440. Each hole 1440 has four columns of thread segments 1542 and can advantageously receive any one of a non-locking, locking, or variable-angle locking bone screw.

Figure 50:
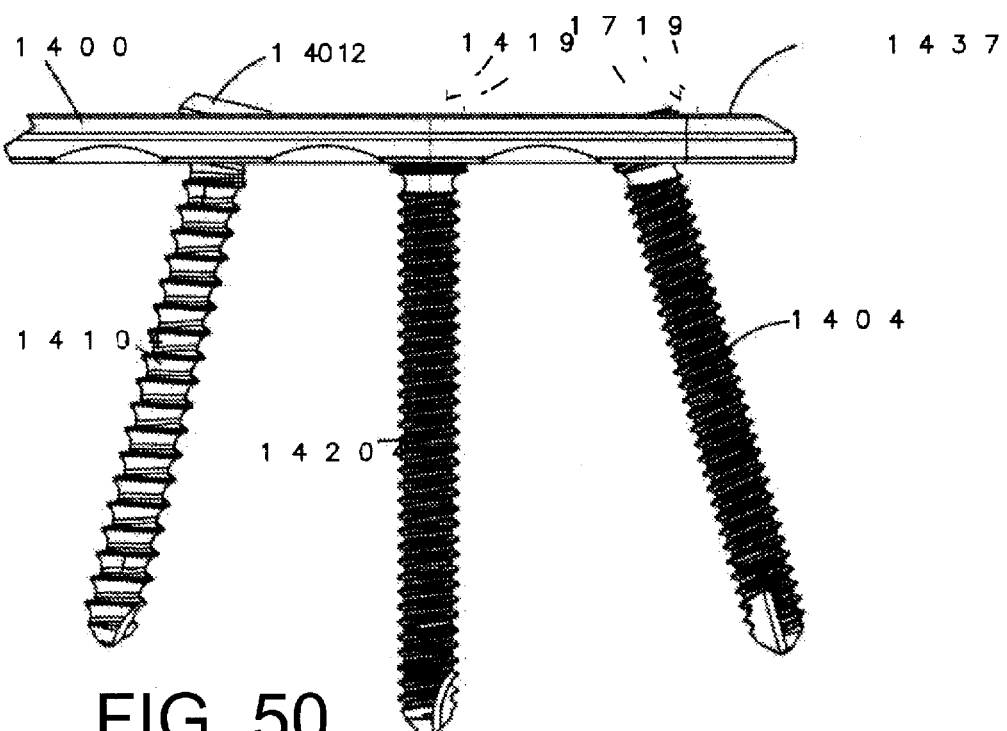
FIG. 50 is an elevation view of the bone plate system of FIG. 49.
Figure 51:
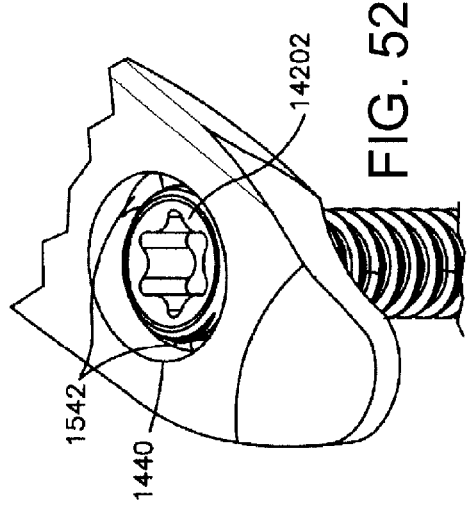
FIG. 51 is a perspective view of a non-locking screw inserted through a bone plate hole according to the invention.
Figure 52:
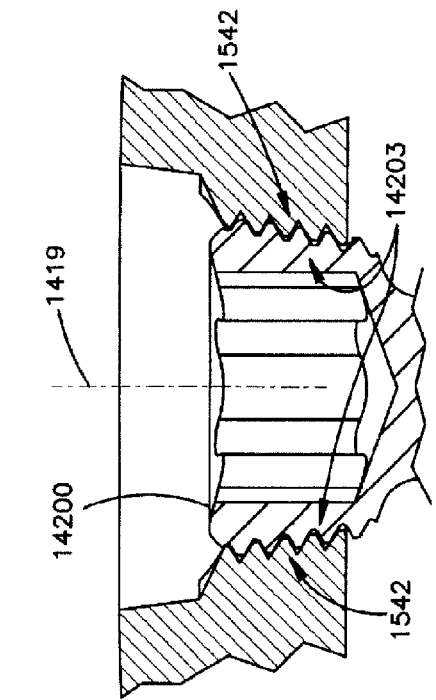
FIG. 52 is an elevation view of the non-locking screw of FIG. 51.
Figure 53:
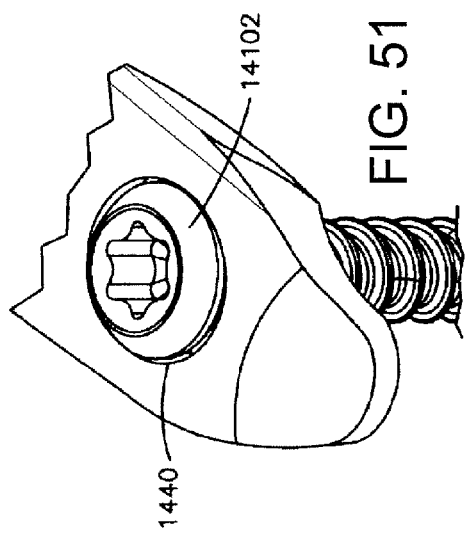
FIG. 53 is a perspective view of a locking screw driven into a bone plate hole according to the invention.
Figure 54:
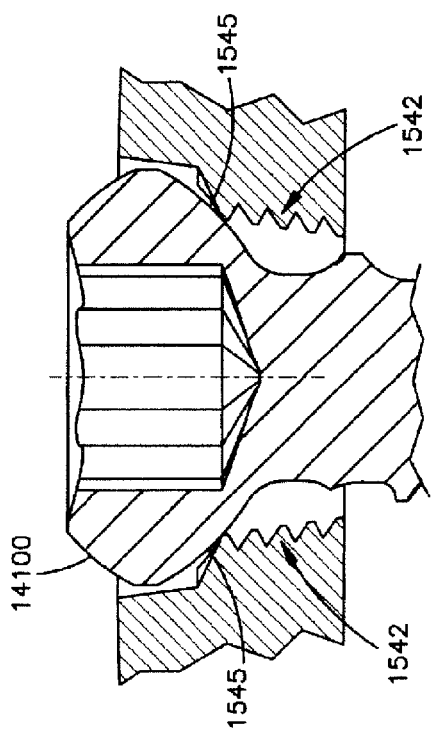
FIG. 54 is an elevation view of the locking screw of FIG. 53.
Figure 55:
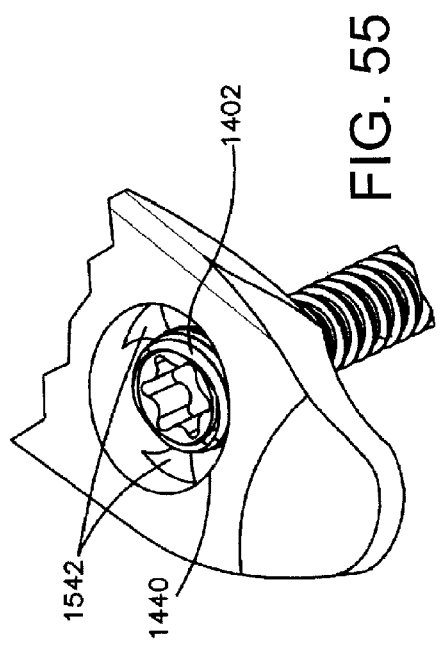
FIG. 55 is a perspective view of a variable-angle locking screw driven into a bone plate hole according to the invention.
Figure 56:
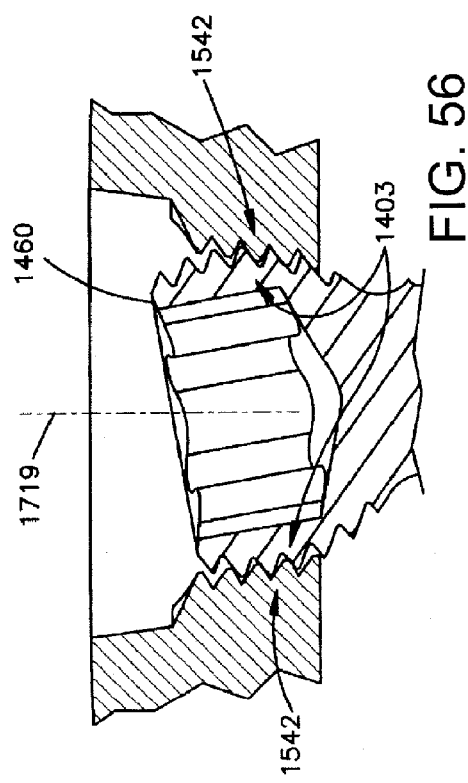
FIG. 56 is an elevation view of the variable-angle locking screw of FIG. 55.

As shown in FIGS. 49, 50, 51 and 53, a conventional non-locking bone screw 14100 can be inserted through one of bone plate holes 1440. Non-locking bone screw 14100 has a non-threaded screwhead 14102 and a threaded shank 14104, each appropriately sized and configured for use with hole 1440. Note that non-locking bone screw 14100 does not have to be inserted through hole 1440 coaxially with the central axis of the hole, but may instead be inserted through hole 1440 at a selectable angle, as shown in FIG. 50. FIG. 53 shows that screwhead 14102 does not engage the columns of thread segments 1542, but instead contacts shoulder 1545 of hole 1440 when fully seated therein.

FIGS. 49, 50, 52, and 54 show conventional locking bone screw 14200 inserted though a second bone plate hole 1440. Locking bone screw 14200 has a screwhead 14202 with a thread 14203 on an outer surface therefore. Both the screwhead and thread are appropriately sized and dimensioned such that thread 14203 can threadingly engage and mate with columns of thread segments 1542. In order to properly engage and mate with columns of thread segments 1542, locking bone screw 14200 should be inserted through hole 1440 coaxially with central axis 1419 of the hole. Screw 14200 also has a threaded shank 14204 for engaging bone. Shank 14204 is also appropriately sized and dimensioned for insertion through hole 1440.

FIGS. 49, 50, 55 and 56 show variable-angle locking bone screw 1460 inserted through a third bone plate hole 1440. Variable-angle locking bone screw 1460, constructed in accordance with the invention, has a threaded shank 1404 and a partially-spherical head 1402 with thread 1403 on an outer surface thereof. Screwhead thread 1403 has a profile that advantageously follows the arc-shaped (i.e., non-linear) radius of curvature of the spherically-shaped portion of head 1402. Screw 1460 is shown inserted into the third hole 1440 non-coaxially with the central axis 1719 with thread 1403 securely engaging columns of thread segments 1542.

Figure 57:
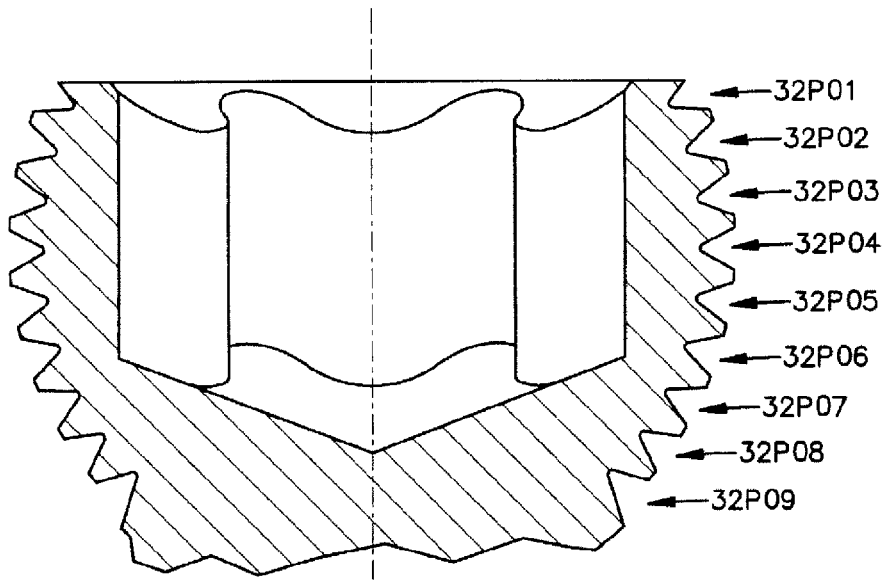
FIG. 57 is a cross-sectional view of a first embodiment of a screwhead of a variable-angle locking bone screw according to the invention.
Figure 58:
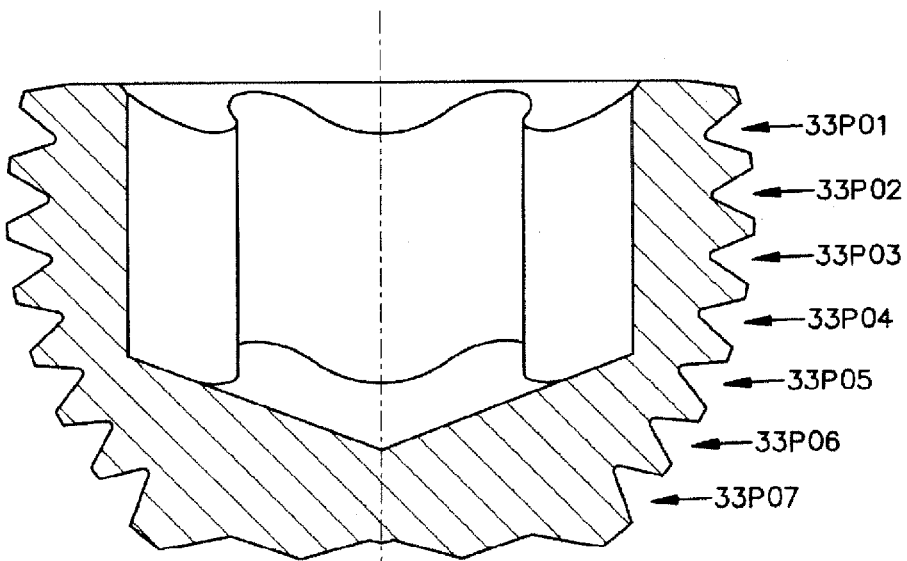
FIG. 58 is a cross-sectional view of a second embodiment of a screwhead of a variable-angle locking bone screw according to the invention.
Figure 59:
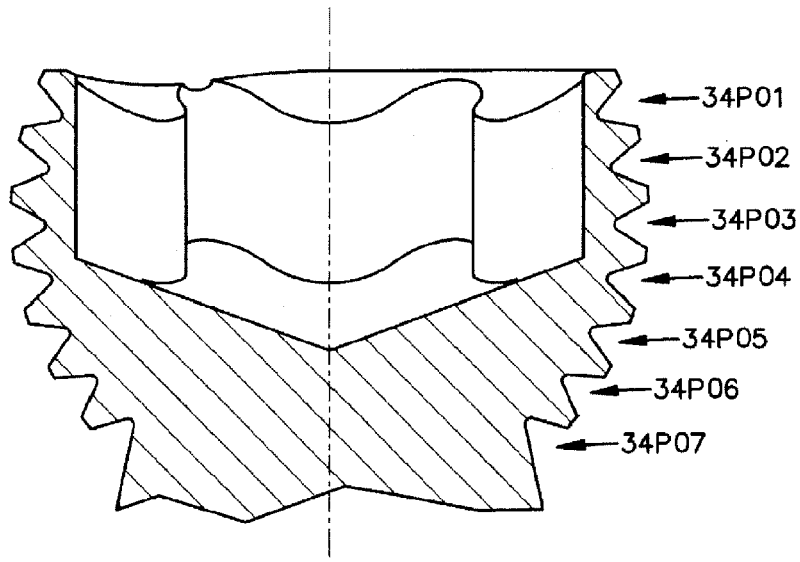
FIG. 59 is a cross-sectional view of a third embodiment of a screwhead of a variable-angle locking bone screw according to the invention.

Returning to the screwhead thread features of variable-angle locking bone screws constructed in accordance with the invention, FIGS. 57-59 show three embodiments of a variable-angle locking screw screwhead that illustrate the varying thread pitches (e.g., the peak to peak distance) as measured along the central axis of each screw. The following table lists the size of the variable-angle screw to which the illustrated screwhead belongs and the varying pitches (all dimensions in millimeters).

|  | FIG. 57 | FIG. 58 | FIG. 59 |
| --- | --- | --- | --- |
| Shaft diameter: | 5.0 | 3.5 | 2.4 |
| Screwhead diameter: | 6.5 | 4.5 | 3.0 |
| Pitch: | 32P01 = 0.90 | 33P01 = 0.76 | 34P01 = 0.56 |
|  | 32P02 = 0.95 | 33P02 = 0.79 | 34P02 = 0.59 |
|  | 32P03 = 0.99 | 33P03 = 0.80 | 34P03 = 0.60 |
|  | 32P04 = 1.00 | 33P04 = 0.79 | 34P04 = 0.58 |
|  | 32P05 = 0.99 | 33P05 = 0.75 | 34P05 = 0.55 |
|  | 32P06 = 0.95 | 33P06 = 0.68 | 34P06 = 0.49 |
|  | 32P07 = 0.90 | 33P07 = 0.60 | 34P07 = 0.41 |
|  | 32P08 = 0.82 |  |  |
|  | 32P09 = 0.72 |  |  |

Other embodiments of variable-angle locking bone screws of the invention may have other varying thread pitches.

Figure 60:
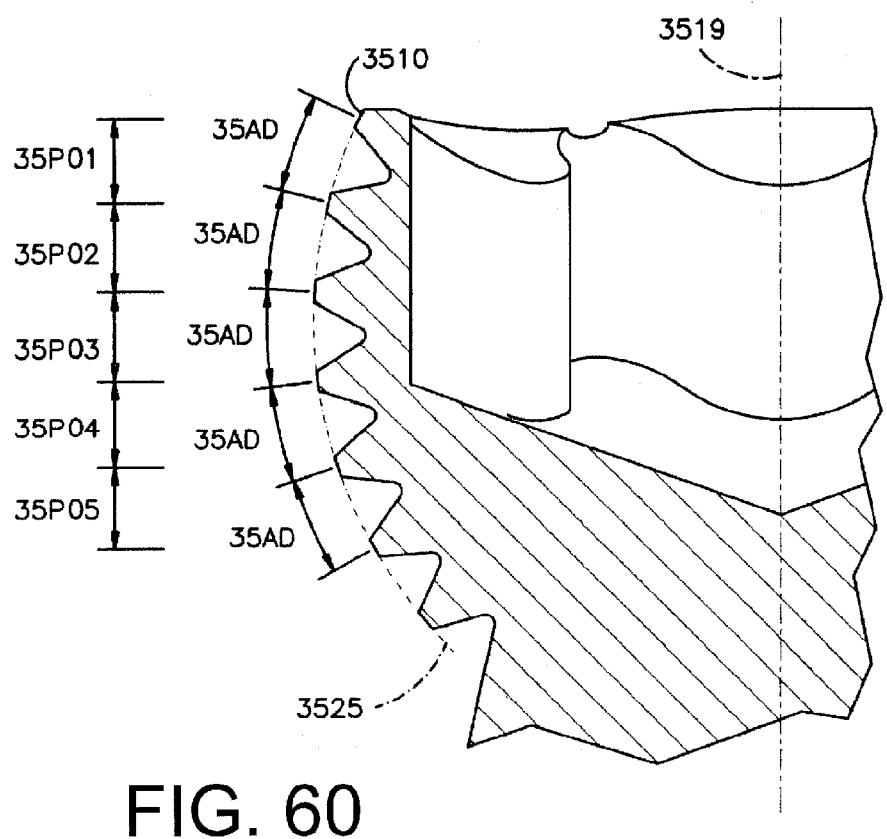
FIG. 60 is an enlarged partial cross-sectional view of a screwhead of a variable-angle locking bone screw according to the invention.

Note that in each case, the angular distance between adjacent thread peaks (or adjacent thread troughs) as measured along the radius of curvature is constant, as illustrated in FIG. 60. That is, each angular distance 35AD between adjacent thread peaks 3510 as measured along the radius of curvature 3525 is the same--in contrast to thread pitches 35P01-35P05 which, as illustrated in FIGS. 57-59, vary as measured along or parallel to central axis 3519.

It will be apparent to those skilled in the art that various modifications and variations can be made in the structure and the methodology of the present invention without departing from the spirit or scope of the invention. Specifically, the features and illustrations described herein may be used singularly or in any combination with other features and embodiments. Thus, it is intended that the present invention cover the modifications and variations of this invention provided that they come within the scope of the appended claims and their equivalents.

What is claimed is:

1. A system for bone fixation, comprising:
an elongated bone implant having a shaft configured for insertion into a bone in an operative configuration and being formed of a ferrite-free implant grade material, an outer surface of the bone implant being one of carburized and nitrided to have a first hardness and to increase a corrosion resistance; and
a bone fixation plate having an opening extending therethrough from a first surface configured to contact the bone in an operative configuration to a second surface located opposite the first surface, the opening being configured to receive the bone implant therethrough, the bone fixation plate having a second hardness;
wherein the first hardness is greater than the second hardness.

2. The system of claim 1, wherein the bone implant is a bone screw having a threaded head.

3. The system of claim 1, wherein a head of the bone implant includes a rounded outer profile.

4. The system of claim 1, wherein a head of the implant includes a substantially spherical outer profile.

5. The system of claim 1, wherein the opening is a variable angle hole.

6. The system of claim 1, wherein the first hardness in the range of 67-74 HRC and the second hardness is in the range of 74 HRB-44 HRC.

7. The system of claim 1, wherein the bone implant is formed of one of an implant quality austensitic stainless steel, cobalt alloys, MP35N, L605, ASTM-F-1058,Elgiloy, Titanium, and titanium alloys.

8. The system of claim 7, wherein the bone implant is formed of one of Biodur 108 and 316L stainless steel.

9. A bone fixation element comprising a threaded head and a shaft extending along a longitudinal axis from a proximal end to a distal end and formed of a ferrite-free implant grade material, an outer surface of the head being one of carburized and nitrided to increase a surface hardness thereof and including a first groove extending into the outer surface of the head along a path interrupting the threading and extending along an angle counter to an angle of the threading.

10. The bone fixation element of claim 9, wherein a material of the bone fixation element is selected to be harder than a material of a bone plate through which the bone fixation element is to be inserted.

11. The bone fixation element of claim 9, wherein the first groove extends along a groove axis perpendicular to the longitudinal axis of the bone fixation element.

12. The bone fixation element of claim 9, further comprising a notch formed adjacent the distal end of the shaft.

13. The bone fixation element of claim 9, further comprising a recess in a proximal end of the bone fixation element, the recess configured to engage a driving mechanism.

14. The bone fixation element of claim 9, wherein the head comprises one of five grooves and eight grooves.

15. The bone fixation element of claim 9, wherein the shaft is threaded.

16. The bone fixation element of claim 15, wherein a pitch of threads of the shaft is the same as a pitch of threads of the head.

17. The bone fixation element of claim 15, wherein the thread of the shaft includes multiple leads.

18. The bone fixation device of claim 9, wherein the head is substantially spherical.

19. A bone fixation system, comprising:
a bone fixation element comprising a threaded head and a shaft extending along a longitudinal axis from a proximal end to a distal end and being formed of a ferrite-free implant garde material, an outer surface of the head being one of carburized and nitrided to increase a surface hardness thereof and including a first groove extending into the outer surface of the head along a path interrupting the threading and extending along an angle counter to an angle of the threading; and
an elongated bone plate extending along a plate axis and having a plate hole extending therethrough from a first surface to a second surface configured to contact a bone in an operative configuration.

20. The bone fixation system of claim 19, wherein a material of the bone fixation element is selected to be harder than a material of the bone plate through which the bone fixation element is to be inserted.

21. The bone fixation system of claim 19, wherein the first groove extends along a groove axis perpendicular to the longitudinal axis of the bone fixation element.

22. The bone fixation system of claim 19, wherein the plate hole is one of a combination hole and a variable angle hole.

23. The bone fixation system of claim 19, wherein the second surface of the bone plate comprises a plurality of undercuts.

24. The bone fixation system of claim 19, wherein the plate hole comprises a first tapered portion adjacent the first surface, a second tapered portion adjacent the second surface and a threaded portion extending between the first and second tapered portions.

25. The bone fixation system of claim 19, further comprising a notch adjacent the distal end of the bone screw.

26. The bone fixation system of claim 19, further comprising a recess in a proximal end of the bone screw, the recess configured to engage a driving mechanism.

27. The bone fixation system of claim 19, wherein the shaft is threaded.

28. The bone fixation system of claim 19, wherein a pitch of threads of the shaft is the same as a pitch of threads of the head.

29. The bone fixation system of claim 19, wherein the plate hole is a variable angle hole including a slot extending along a wall of the hole and configured to interrupt threads thereof.

30. A method for treating a bone, comprising:
placing a bone fixation device over a target bone, the bone fixation device extending along a plate axis and having a hole extending therethrough from a first surface to a second surface configured to contact the bone in an operative configuration; and
inserting a bone fixation element through the hole and into the bone, the bone fixation element comprising a threaded head and a shaft extending along a longitudinal axis from a proximal end to a distal end and being formed of a ferrite-free implant grade material, an outer surface of the head being one of carburized and nitrided to increase a surface hardness thereof and including a first groove extending into the outer surface of the head along a path interrupting the threading and extending along an angle counter to an angle of the threading.

* * * * *